United States Patent
Choi et al.

(10) Patent No.: US 12,270,061 B2
(45) Date of Patent: Apr. 8, 2025

(54) MODIFIED POLYPEPTIDE OF GLUTAMINE SYNTHETASE AND METHOD OF PRODUCING L-GLUTAMINE USING THE SAME

(71) Applicant: CJ CHEILJEDANG CORPORATION, Seoul (KR)

(72) Inventors: Su Jin Choi, Seoul (KR); Imsang Lee, Seoul (KR); Heeyeong Kim, Seoul (KR); Byeong Soo Kim, Seoul (KR); Kwang Woo Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 199 days.

(21) Appl. No.: 17/604,896

(22) PCT Filed: Mar. 4, 2021

(86) PCT No.: PCT/KR2021/002652
§ 371 (c)(1),
(2) Date: Oct. 19, 2021

(87) PCT Pub. No.: WO2021/177731
PCT Pub. Date: Sep. 10, 2021

(65) Prior Publication Data
US 2022/0396815 A1    Dec. 15, 2022

(30) Foreign Application Priority Data
Mar. 4, 2020 (KR) .................. 10-2020-0027322

(51) Int. Cl.
| | |
|---|---|
| *C12P 13/14* | (2006.01) |
| *C12N 9/00* | (2006.01) |
| *C12N 15/10* | (2006.01) |
| *C12N 15/77* | (2006.01) |
| *C12R 1/15* | (2006.01) |
| *C40B 40/02* | (2006.01) |
| *C40B 40/10* | (2006.01) |

(52) U.S. Cl.
CPC ............... *C12P 13/14* (2013.01); *C12N 9/93* (2013.01); *C12N 15/77* (2013.01); *C40B 40/10* (2013.01); *C12N 15/1034* (2013.01); *C12R 2001/15* (2021.05); *C40B 40/02* (2013.01)

(58) Field of Classification Search
CPC ..... C12P 13/14; C12N 15/77; C12R 2001/15; C12Y 603/01002
See application file for complete search history.

(56) References Cited

U.S. PATENT DOCUMENTS

| | | | | |
|---|---|---|---|---|
| 2006/0269975 A1* | 11/2006 | Pompejus | ........ | G01N 33/56911 435/106 |
| 2017/0051323 A1* | 2/2017 | Ochrombel | .... | C12Y 305/03013 |

FOREIGN PATENT DOCUMENTS

| | | |
|---|---|---|
| CN | 100392075 C | 6/2008 |
| EP | 1 460 128 A1 | 9/2004 |
| EP | 1 229 121 B1 | 1/2006 |
| JP | 2002-300887 A | 10/2002 |
| JP | 2003-164297 A | 6/2003 |
| JP | 2004-187684 A | 7/2004 |
| JP | 2004-283167 A | 10/2004 |
| KR | 10-2013-0105380 A | 9/2013 |
| KR | 10-2198072 B1 | 12/2020 |

OTHER PUBLICATIONS

Encyclopedia Britannica, "homology" 2015, pp. 1-2, available at https://www.britannica.com/print/article/270557 (Year: 2015).*
Samudrala, R., 2015, p. 1 "Difference Between Homology, Identity, and Similarity," available online at http://www.bio.net/mm/proteins/1998-July/006538.html. (Year: 2015).*
Pearson, W., 2013, Curr Protoc Bioinformatics. p. 1-9 (Year: 2013).*
Kanduc, D., 2012, J. Pept. Sci. 18:487-494 (Year: 2012).*
GenBank: AJE32350.1, Citrate Synthase [Corynebacterium humireducens NBRC 106098 = DSM 45392], pp. 1-2. (Year: 2013).*
ENA, Sequence CP005286.1, Corynebacterium humireducens NBRC 106098, DSM 45392, pp. 1-19 (Year: 2019).*
Ochrombel et al., U.S. Appl. No. 11/370,121, Amino Acid Seq Id No. 216 Ribonuclease III EC 3.1.26.3 (Year: 2006).*
Ochrombel et al., U.S. Appl. No. 11/370,121, Amino Acid Seq Id No. 248 DNA Helicase II EC 3.6.1 (Year: 2006).*
Ochrombel et al., U.S. Appl. No. 11/370,121, Nucleic Acid Seq Id No. 215 Ribonuclease III EC 3.1.26.3 (Year: 2006).*
Ochrombel et al., U.S. Appl. No. 11/370,121, Nuceic Acid Seq Id No. 247 DNA Helicase II EC 3.6.1 (Year: 2006).*
UniProt, Ribonuclease 3, Corynebacterium glutamicum strain ATCC 13032 (Year: 2002).*
MicrobesOnline, dnaB Replicative Helicase, Corynebacterium glutamicum ATCC 13032 (EC 3.6.1), pp. 1-2. (Year: 2009).*
Liu et al. Appl Microbiol Biotechnol (2008) 77:1297-1304, pp. 1297-1304. (Year: 2008).*
Hauer "Sequencing of glnA gene of mutants HM14, HM26, HM053 and HM210 of *Azospirillum brasilense*," Monography submitted as pre-requirement for concluding the Biological Sciences Course, Bachelor's Degree, of the Federal University of Paraná. Curitiba, 2012, 49 pages, https://hdl.handle.net/1884/30659, with English abstract.
Ye, GenBank: UUP14975, type I glutamate-ammonia ligase [*Aeromicrobium* sp. Zg. Y1379] 2 pages, (Aug. 8, 2022).

(Continued)

*Primary Examiner* — Lianko G Garyu
*Assistant Examiner* — Claudia Espinosa
(74) *Attorney, Agent, or Firm* — Seed IP Law Group LLP

(57) ABSTRACT

The present disclosure relates to a modified polypeptide of glutamine synthetase having enhanced activity and a method of producing L-glutamine using the same. Since production of L-glutamine may be increased by using the novel modified polypeptide without a decrease in a growth rate compared to wild-type strains having glutamine synthetase activity, the modified polypeptide may be widely used for mass production of L-glutamine.

15 Claims, No Drawings

Specification includes a Sequence Listing.

(56) References Cited

OTHER PUBLICATIONS

GenBank: AAD01244.2, "glutamine synthetase [Corynebacterium glutamicum]" (1 page) Jun. 14, 1999.

Huang et al., "Expression of site-directed mutant glutamine synthetase and enzymatic glutamine production," *Journal of Chemical Industry and Engineering* (*China*) 59(6), 6 pages (with English abstract) (Jun. 2008).

* cited by examiner

SEQUENCE LISTING

<160> NUMBER OF SEQ ID NOS: 29

<210> SEQ ID NO 1
<211> LENGTH: 477
<212> TYPE: PRT

<213> ORGANISM: Artificial Sequence
<220> FEATURE:
<223> OTHER INFORMATION: Synthetic sequence Corynebacterium glutamicum ATCC13032 Glutamine synthetase a.a.

<400> SEQUENCE: 1

```
Val Ala Phe Glu Thr Pro Glu Glu Ile Val Lys Phe Ile Lys Asp Glu
1               5                   10                  15

Asn Val Glu Phe Val Asp Val Arg Phe Thr Asp Leu Pro Gly Thr Glu
            20                  25                  30

Gln His Phe Ser Ile Pro Ala Ala Ser Phe Asp Ala Asp Thr Ile Glu
        35                  40                  45

Glu Gly Leu Ala Phe Asp Gly Ser Ser Ile Arg Gly Phe Thr Thr Ile
    50                  55                  60

Asp Glu Ser Asp Met Asn Leu Leu Pro Asp Leu Gly Thr Ala Thr Leu
65                  70                  75                  80

Asp Pro Phe Arg Lys Ala Lys Thr Leu Asn Val Lys Phe Phe Val His
                85                  90                  95

Asp Pro Phe Thr Arg Glu Ala Phe Ser Arg Asp Pro Arg Asn Val Ala
            100                 105                 110

Arg Lys Ala Glu Gln Tyr Leu Ala Ser Thr Gly Ile Ala Asp Thr Cys
        115                 120                 125

Asn Phe Gly Ala Glu Ala Glu Phe Tyr Leu Phe Asp Ser Val Arg Tyr
    130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
                165                 170                 175

Gly Ala Lys Asn Arg Val Lys Gly Gly Tyr Phe Pro Val Ala Pro Tyr
            180                 185                 190

Asp Gln Thr Val Asp Val Arg Asp Asp Met Val Arg Asn Leu Ala Ala
        195                 200                 205

Ser Gly Phe Ala Leu Glu Arg Phe His His Glu Val Gly Gly Gly Gln
    210                 215                 220

Gln Glu Ile Asn Tyr Arg Phe Asn Thr Met Leu His Ala Ala Asp Asp
225                 230                 235                 240

Ile Gln Thr Phe Lys Tyr Ile Ile Lys Asn Thr Ala Arg Leu His Gly
                245                 250                 255

Lys Ala Ala Thr Phe Met Pro Lys Pro Leu Ala Gly Asp Asn Gly Ser
            260                 265                 270

Gly Met His Ala His Gln Ser Leu Trp Lys Asp Gly Lys Pro Leu Phe
        275                 280                 285

His Asp Glu Ser Gly Tyr Ala Gly Leu Ser Asp Ile Ala Arg Tyr Tyr
    290                 295                 300

Ile Gly Gly Ile Leu His His Ala Gly Ala Val Leu Ala Phe Thr Asn
305                 310                 315                 320

Ala Thr Leu Asn Ser Tyr His Arg Leu Val Pro Gly Phe Glu Ala Pro
                325                 330                 335

Ile Asn Leu Val Tyr Ser Gln Arg Asn Arg Ser Ala Ala Val Arg Ile
            340                 345                 350

Pro Ile Thr Gly Ser Asn Pro Lys Ala Lys Arg Ile Glu Phe Arg Ala
        355                 360                 365

Pro Asp Pro Ser Gly Asn Pro Tyr Leu Gly Phe Ala Ala Met Met Met
    370                 375                 380
```

```
Ala Gly Leu Asp Gly Ile Lys Asn Arg Ile Glu Pro His Ala Pro Val
385                 390                 395                 400

Asp Lys Asp Leu Tyr Glu Leu Pro Pro Glu Glu Ala Ala Ser Ile Pro
            405                 410                 415

Gln Ala Pro Thr Ser Leu Glu Ala Ser Leu Lys Ala Leu Gln Glu Asp
            420                 425                 430

Thr Asp Phe Leu Thr Glu Ser Asp Val Phe Thr Glu Asp Leu Ile Glu
        435                 440                 445

Ala Tyr Ile Gln Tyr Lys Tyr Asp Asn Glu Ile Ser Pro Val Arg Leu
        450                 455                 460

Arg Pro Thr Pro Gln Glu Phe Glu Leu Tyr Phe Asp Cys
465                 470                 475
```

<210> SEQ ID NO 2
<211> LENGTH: 477
<212> TYPE: PRT
<213> ORGANISM: Artificial Sequence
<220> FEATURE:
<223> OTHER INFORMATION: Synthetic sequence Corynebacterium glutamicum
    ATCC13032 Glutamine synthetase variant a.a.

<400> SEQUENCE: 2

```
Val Ala Phe Glu Thr Pro Glu Glu Ile Val Lys Phe Ile Lys Asp Glu
1               5                   10                  15

Asn Val Glu Phe Val Asp Val Arg Phe Thr Asp Leu Pro Gly Thr Glu
            20                  25                  30

Gln His Phe Ser Ile Pro Ala Ala Ser Phe Asp Ala Asp Thr Ile Glu
        35                  40                  45

Glu Gly Leu Ala Phe Asp Gly Ser Ser Ile Arg Gly Phe Thr Thr Ile
50                  55                  60

Asp Glu Ser Asp Met Asn Leu Leu Pro Asp Leu Gly Thr Ala Thr Leu
65                  70                  75                  80

Asp Pro Phe Arg Lys Ala Lys Thr Leu Asn Val Lys Phe Phe Val His
                85                  90                  95

Asp Pro Phe Thr Arg Glu Ala Phe Ser Arg Asp Pro Arg Asn Val Ala
            100                 105                 110

Arg Lys Ala Glu Gln Tyr Leu Ala Ser Thr Gly Ile Ala Asp Thr Cys
        115                 120                 125

Asn Phe Gly Ala Glu Ala Glu Phe Tyr Leu Phe Asp Ser Val Arg Tyr
130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
                165                 170                 175

Gly Ala Lys Asn Arg Val Lys Gly Gly Tyr Phe Pro Val Ala Pro Tyr
            180                 185                 190

Asp Gln Thr Val Asp Val Arg Asp Asp Met Val Arg Asn Leu Ala Ala
        195                 200                 205

Ser Gly Phe Ala Leu Glu Arg Phe His His Glu Val Gly Gly Gly Gln
210                 215                 220

Gln Glu Ile Asn Tyr Arg Phe Asn Thr Met Leu His Ala Ala Asp Asp
225                 230                 235                 240

Ile Gln Thr Phe Lys Tyr Ile Ile Lys Asn Thr Ala Arg Leu His Gly
                245                 250                 255

Lys Ala Ala Thr Phe Met Pro Lys Pro Leu Ala Gly Asp Asn Gly Ser
            260                 265                 270
```

```
Gly Met His Ala His Gln Ser Leu Trp Lys Asp Gly Lys Pro Leu Phe
            275                 280                 285

His Asp Glu Ser Gly Tyr Ala Gly Leu Ser Asp Ile Ala Arg Tyr Tyr
        290                 295                 300

Ile Gly Gly Ile Leu His His Ala Gly Ala Val Leu Ala Phe Thr Asn
305                 310                 315                 320

Ala Thr Leu Asn Ser Tyr His Arg Leu Val Pro Gly Phe Glu Ala Pro
                325                 330                 335

Ile Asn Leu Val Tyr Ser Gln Arg Asn Arg Ser Ala Ala Val Arg Ile
            340                 345                 350

Pro Ile Thr Gly Ser Asn Pro Lys Ala Lys Arg Ile Glu Phe Arg Ala
        355                 360                 365

Pro Asp Pro Ser Gly Asn Pro Tyr Leu Gly Phe Ala Ala Met Met Met
    370                 375                 380

Ala Gly Leu Asp Gly Ile Lys Asn Arg Ile Glu Pro His Ala Pro Val
385                 390                 395                 400

Asn Lys Asp Leu Tyr Glu Leu Pro Pro Glu Glu Ala Ala Ser Ile Pro
                405                 410                 415

Gln Ala Pro Thr Ser Leu Glu Ala Ser Leu Lys Ala Leu Gln Glu Asp
            420                 425                 430

Thr Asp Phe Leu Thr Glu Ser Asp Val Phe Thr Glu Asp Leu Ile Glu
        435                 440                 445

Ala Tyr Ile Gln Tyr Lys Tyr Asp Asn Glu Ile Ser Pro Val Arg Leu
    450                 455                 460

Arg Pro Thr Pro Gln Glu Phe Glu Leu Tyr Phe Asp Cys
465                 470                 475

<210> SEQ ID NO 3
<211> LENGTH: 477
<212> TYPE: PRT
<213> ORGANISM: Artificial Sequence
<220> FEATURE:
<223> OTHER INFORMATION: Synthetic sequence Corynebacterium glutamicum
      ATCC13032 Glutamine synthetase variant a.a.

<400> SEQUENCE: 3

Val Ala Phe Glu Thr Pro Glu Glu Ile Val Lys Phe Ile Lys Asp Glu
1               5                   10                  15

Asn Val Glu Phe Val Asp Val Arg Phe Thr Asp Leu Pro Gly Thr Glu
            20                  25                  30

Gln His Phe Ser Ile Pro Ala Ala Ser Phe Asp Ala Asp Thr Ile Glu
        35                  40                  45

Glu Gly Leu Ala Phe Asp Gly Ser Ser Ile Arg Gly Phe Thr Thr Ile
    50                  55                  60

Asp Glu Ser Asp Met Asn Leu Leu Pro Asp Leu Gly Thr Ala Thr Leu
65                  70                  75                  80

Asp Pro Phe Arg Lys Ala Lys Thr Leu Asn Val Lys Phe Phe Val His
                85                  90                  95

Asp Pro Phe Thr Arg Glu Ala Phe Ser Arg Asp Pro Arg Asn Val Ala
            100                 105                 110

Arg Lys Ala Glu Gln Tyr Leu Ala Ser Thr Gly Ile Ala Asp Thr Cys
        115                 120                 125

Asn Phe Gly Ala Glu Ala Glu Phe Tyr Leu Phe Asp Ser Val Arg Tyr
    130                 135                 140

Ser Thr Glu Met Asn Ser Gly Phe Tyr Glu Val Asp Thr Glu Glu Gly
```

```
            145                 150                 155                 160

Trp Trp Asn Arg Gly Lys Glu Thr Asn Leu Asp Gly Thr Pro Asn Leu
                        165                 170                 175

Gly Ala Lys Asn Arg Val Lys Gly Gly Tyr Phe Pro Val Ala Pro Tyr
                        180                 185                 190

Asp Gln Thr Val Asp Val Arg Asp Met Val Arg Asn Leu Ala Ala
                        195                 200                 205

Ser Gly Phe Ala Leu Glu Arg Phe His His Glu Val Gly Gly Gln
                210                 215                 220

Gln Glu Ile Asn Tyr Arg Phe Asn Thr Met Leu His Ala Ala Asp Asp
        225                 230                 235                 240

Ile Gln Thr Phe Lys Tyr Ile Ile Lys Asn Thr Ala Arg Leu His Gly
                        245                 250                 255

Lys Ala Ala Thr Phe Met Pro Lys Pro Leu Ala Gly Asp Asn Gly Ser
                        260                 265                 270

Gly Met His Ala His Gln Ser Leu Trp Lys Asp Gly Lys Pro Leu Phe
                        275                 280                 285

His Asp Glu Ser Gly Tyr Ala Gly Leu Ser Asp Ile Ala Arg Tyr Tyr
                        290                 295                 300

Ile Gly Gly Ile Leu His His Ala Gly Ala Val Leu Ala Phe Thr Asn
        305                 310                 315                 320

Ala Thr Leu Asn Ser Tyr His Arg Leu Val Pro Gly Phe Glu Ala Pro
                        325                 330                 335

Ile Asn Leu Val Tyr Ser Gln Arg Asn Arg Ser Ala Ala Val Arg Ile
                        340                 345                 350

Pro Ile Thr Gly Ser Asn Pro Lys Ala Lys Arg Ile Glu Phe Arg Ala
                        355                 360                 365

Pro Asp Pro Ser Gly Asn Pro Tyr Leu Gly Phe Ala Ala Met Met Met
                        370                 375                 380

Ala Gly Leu Asp Gly Ile Lys Asn Arg Ile Glu Pro His Ala Pro Val
        385                 390                 395                 400

Glu Lys Asp Leu Tyr Glu Leu Pro Pro Glu Glu Ala Ala Ser Ile Pro
                        405                 410                 415

Gln Ala Pro Thr Ser Leu Glu Ala Ser Leu Lys Ala Leu Gln Glu Asp
                        420                 425                 430

Thr Asp Phe Leu Thr Glu Ser Asp Val Phe Thr Glu Asp Leu Ile Glu
                        435                 440                 445

Ala Tyr Ile Gln Tyr Lys Tyr Asp Asn Glu Ile Ser Pro Val Arg Leu
                        450                 455                 460

Arg Pro Thr Pro Gln Glu Phe Glu Leu Tyr Phe Asp Cys
        465                 470                 475

<210> SEQ ID NO 4
<211> LENGTH: 477
<212> TYPE: PRT
<213> ORGANISM: Artificial Sequence
<220> FEATURE:
<223> OTHER INFORMATION: Synthetic sequence Corynebacterium glutamicum
      ATCC13032 Glutamine synthetase variant a.a.

<400> SEQUENCE: 4

Val Ala Phe Glu Thr Pro Glu Glu Ile Val Lys Phe Ile Lys Asp Glu
1               5                   10                  15

Asn Val Glu Phe Val Asp Val Arg Phe Thr Asp Leu Pro Gly Thr Glu
                20                  25                  30
```

```
Gln His Phe Ser Ile Pro Ala Ala Ser Phe Asp Ala Asp Thr Ile Glu
         35                  40                  45

Glu Gly Leu Ala Phe Asp Gly Ser Ile Arg Gly Phe Thr Thr Ile
 50                  55                  60

Asp Glu Ser Asp Met Asn Leu Leu Pro Asp Leu Gly Thr Ala Thr Leu
 65                  70                  75                  80

Asp Pro Phe Arg Lys Ala Lys Thr Leu Asn Val Lys Phe Phe Val His
                 85                  90                  95

Asp Pro Phe Thr Arg Glu Ala Phe Ser Arg Asp Pro Arg Asn Val Ala
                100                 105                 110

Arg Lys Ala Glu Gln Tyr Leu Ala Ser Thr Gly Ile Ala Asp Thr Cys
            115                 120                 125

Asn Phe Gly Ala Glu Ala Glu Phe Tyr Leu Phe Asp Ser Val Arg Tyr
        130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
                165                 170                 175

Gly Ala Lys Asn Arg Val Lys Gly Gly Tyr Phe Pro Val Ala Pro Tyr
                180                 185                 190

Asp Gln Thr Val Asp Val Arg Asp Asp Met Val Arg Asn Leu Ala Ala
            195                 200                 205

Ser Gly Phe Ala Leu Glu Arg Phe His His Glu Val Gly Gly Gly Gln
        210                 215                 220

Gln Glu Ile Asn Tyr Arg Phe Asn Thr Met Leu His Ala Ala Asp Asp
225                 230                 235                 240

Ile Gln Thr Phe Lys Tyr Ile Ile Lys Asn Thr Ala Arg Leu His Gly
                245                 250                 255

Lys Ala Ala Thr Phe Met Pro Lys Pro Leu Ala Gly Asp Asn Gly Ser
                260                 265                 270

Gly Met His Ala His Gln Ser Leu Trp Lys Asp Gly Lys Pro Leu Phe
            275                 280                 285

His Asp Glu Ser Gly Tyr Ala Gly Leu Ser Asp Ile Ala Arg Tyr Tyr
        290                 295                 300

Ile Gly Gly Ile Leu His His Ala Gly Ala Val Leu Ala Phe Thr Asn
305                 310                 315                 320

Ala Thr Leu Asn Ser Tyr His Arg Leu Val Pro Gly Phe Glu Ala Pro
                325                 330                 335

Ile Asn Leu Val Tyr Ser Gln Arg Asn Arg Ser Ala Ala Val Arg Ile
                340                 345                 350

Pro Ile Thr Gly Ser Asn Pro Lys Ala Lys Arg Ile Glu Phe Arg Ala
            355                 360                 365

Pro Asp Pro Ser Gly Asn Pro Tyr Leu Gly Phe Ala Ala Met Met Met
        370                 375                 380

Ala Gly Leu Asp Gly Ile Lys Asn Arg Ile Glu Pro His Ala Pro Val
385                 390                 395                 400

Ser Lys Asp Leu Tyr Glu Leu Pro Pro Glu Glu Ala Ala Ser Ile Pro
                405                 410                 415

Gln Ala Pro Thr Ser Leu Glu Ala Ser Leu Lys Ala Leu Gln Glu Asp
                420                 425                 430

Thr Asp Phe Leu Thr Glu Ser Asp Val Phe Thr Glu Asp Leu Ile Glu
            435                 440                 445

Ala Tyr Ile Gln Tyr Lys Tyr Asp Asn Glu Ile Ser Pro Val Arg Leu
```

```
                450             455             460
Arg Pro Thr Pro Gln Glu Phe Glu Leu Tyr Phe Asp Cys
465                 470                 475

<210> SEQ ID NO 5
<211> LENGTH: 477
<212> TYPE: PRT
<213> ORGANISM: Artificial Sequence
<220> FEATURE:
<223> OTHER INFORMATION: Synthetic sequence Corynebacterium glutamicum
      ATCC13032 Glutamine synthetase variant a.a.

<400> SEQUENCE: 5

Val Ala Phe Glu Thr Pro Glu Glu Ile Val Lys Phe Ile Lys Asp Glu
1               5                   10                  15

Asn Val Glu Phe Val Asp Val Arg Phe Thr Asp Leu Pro Gly Thr Glu
                20                  25                  30

Gln His Phe Ser Ile Pro Ala Ala Ser Phe Asp Ala Asp Thr Ile Glu
            35                  40                  45

Glu Gly Leu Ala Phe Asp Gly Ser Ser Ile Arg Gly Phe Thr Thr Ile
        50                  55                  60

Asp Glu Ser Asp Met Asn Leu Leu Pro Asp Leu Gly Thr Ala Thr Leu
65                  70                  75                  80

Asp Pro Phe Arg Lys Ala Lys Thr Leu Asn Val Lys Phe Phe Val His
                85                  90                  95

Asp Pro Phe Thr Arg Glu Ala Phe Ser Arg Asp Pro Arg Asn Val Ala
                100                 105                 110

Arg Lys Ala Glu Gln Tyr Leu Ala Ser Thr Gly Ile Ala Asp Thr Cys
            115                 120                 125

Asn Phe Gly Ala Glu Ala Glu Phe Tyr Leu Phe Asp Ser Val Arg Tyr
        130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
                165                 170                 175

Gly Ala Lys Asn Arg Val Lys Gly Gly Tyr Phe Pro Val Ala Pro Tyr
                180                 185                 190

Asp Gln Thr Val Asp Val Arg Asp Asp Met Val Arg Asn Leu Ala Ala
            195                 200                 205

Ser Gly Phe Ala Leu Glu Arg Phe His His Glu Val Gly Gly Gly Gln
        210                 215                 220

Gln Glu Ile Asn Tyr Arg Phe Asn Thr Met Leu His Ala Ala Asp Asp
225                 230                 235                 240

Ile Gln Thr Phe Lys Tyr Ile Ile Lys Asn Thr Ala Arg Leu His Gly
                245                 250                 255

Lys Ala Ala Thr Phe Met Pro Lys Pro Leu Ala Gly Asp Asn Gly Ser
                260                 265                 270

Gly Met His Ala His Gln Ser Leu Trp Lys Asp Gly Lys Pro Leu Phe
            275                 280                 285

His Asp Glu Ser Gly Tyr Ala Gly Leu Ser Asp Ile Ala Arg Tyr Tyr
        290                 295                 300

Ile Gly Gly Ile Leu His His Ala Gly Ala Val Leu Ala Phe Thr Asn
305                 310                 315                 320

Ala Thr Leu Asn Ser Tyr His Arg Leu Val Pro Gly Phe Glu Ala Pro
                325                 330                 335
```

Ile Asn Leu Val Tyr Ser Gln Arg Asn Arg Ser Ala Ala Val Arg Ile
            340                 345                 350

Pro Ile Thr Gly Ser Asn Pro Lys Ala Lys Arg Ile Glu Phe Arg Ala
            355                 360                 365

Pro Asp Pro Ser Gly Asn Pro Tyr Leu Gly Phe Ala Ala Met Met Met
370                 375                 380

Ala Gly Leu Asp Gly Ile Lys Asn Arg Ile Glu Pro His Ala Pro Val
385                 390                 395                 400

Asp His Asp Leu Tyr Glu Leu Pro Pro Glu Ala Ala Ser Ile Pro
            405                 410                 415

Gln Ala Pro Thr Ser Leu Glu Ala Ser Leu Lys Ala Leu Gln Glu Asp
            420                 425                 430

Thr Asp Phe Leu Thr Glu Ser Asp Val Phe Thr Glu Asp Leu Ile Glu
            435                 440                 445

Ala Tyr Ile Gln Tyr Lys Tyr Asp Asn Glu Ile Ser Pro Val Arg Leu
            450                 455                 460

Arg Pro Thr Pro Gln Glu Phe Glu Leu Tyr Phe Asp Cys
465                 470                 475

<210> SEQ ID NO 6
<211> LENGTH: 477
<212> TYPE: PRT
<213> ORGANISM: Artificial Sequence
<220> FEATURE:
<223> OTHER INFORMATION: Synthetic sequence Corynebacterium glutamicum
      ATCC13032 Glutamine synthetase variant a.a.

<400> SEQUENCE: 6

Val Ala Phe Glu Thr Pro Glu Glu Ile Val Lys Phe Ile Lys Asp Glu
1               5                   10                  15

Asn Val Glu Phe Val Asp Val Arg Phe Thr Asp Leu Pro Gly Thr Glu
            20                  25                  30

Gln His Phe Ser Ile Pro Ala Ala Ser Phe Asp Ala Asp Thr Ile Glu
        35                  40                  45

Glu Gly Leu Ala Phe Asp Gly Ser Ser Ile Arg Gly Phe Thr Thr Ile
    50                  55                  60

Asp Glu Ser Asp Met Asn Leu Leu Pro Asp Leu Gly Thr Ala Thr Leu
65                  70                  75                  80

Asp Pro Phe Arg Lys Ala Lys Thr Leu Asn Val Lys Phe Phe Val His
                85                  90                  95

Asp Pro Phe Thr Arg Glu Ala Phe Ser Arg Asp Pro Arg Asn Val Ala
            100                 105                 110

Arg Lys Ala Glu Gln Tyr Leu Ala Ser Thr Gly Ile Ala Asp Thr Cys
        115                 120                 125

Asn Phe Gly Ala Glu Ala Glu Phe Tyr Leu Phe Asp Ser Val Arg Tyr
    130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
                165                 170                 175

Gly Ala Lys Asn Arg Val Lys Gly Gly Tyr Phe Pro Ala Pro Tyr
            180                 185                 190

Asp Gln Thr Val Asp Val Arg Asp Asp Met Val Arg Asn Leu Ala Ala
        195                 200                 205

Ser Gly Phe Ala Leu Glu Arg Phe His His Glu Val Gly Gly Gly Gln
    210                 215                 220

-continued

Gln Glu Ile Asn Tyr Arg Phe Asn Thr Met Leu His Ala Ala Asp Asp
225                 230                 235                 240

Ile Gln Thr Phe Lys Tyr Ile Ile Lys Asn Thr Ala Arg Leu His Gly
            245                 250                 255

Lys Ala Ala Thr Phe Met Pro Lys Pro Leu Ala Gly Asp Asn Gly Ser
        260                 265                 270

Gly Met His Ala His Gln Ser Leu Trp Lys Asp Gly Lys Pro Leu Phe
    275                 280                 285

His Asp Glu Ser Gly Tyr Ala Gly Leu Ser Asp Ile Ala Arg Tyr Tyr
290                 295                 300

Ile Gly Gly Ile Leu His His Ala Gly Ala Val Leu Ala Phe Thr Asn
305                 310                 315                 320

Ala Thr Leu Asn Ser Tyr His Arg Leu Val Pro Gly Phe Glu Ala Pro
                325                 330                 335

Ile Asn Leu Val Tyr Ser Gln Arg Asn Arg Ser Ala Ala Val Arg Ile
            340                 345                 350

Pro Ile Thr Gly Ser Asn Pro Lys Ala Lys Arg Ile Glu Phe Arg Ala
        355                 360                 365

Pro Asp Pro Ser Gly Asn Pro Tyr Leu Gly Phe Ala Ala Met Met Met
    370                 375                 380

Ala Gly Leu Asp Gly Ile Lys Asn Arg Ile Glu Pro His Ala Pro Val
385                 390                 395                 400

Asp Lys Asp Val Tyr Glu Leu Pro Pro Glu Ala Ala Ser Ile Pro
                405                 410                 415

Gln Ala Pro Thr Ser Leu Glu Ala Ser Leu Lys Ala Leu Gln Glu Asp
            420                 425                 430

Thr Asp Phe Leu Thr Glu Ser Asp Val Phe Thr Glu Asp Leu Ile Glu
        435                 440                 445

Ala Tyr Ile Gln Tyr Lys Tyr Asp Asn Glu Ile Ser Pro Val Arg Leu
    450                 455                 460

Arg Pro Thr Pro Gln Glu Phe Glu Leu Tyr Phe Asp Cys
465                 470                 475

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gtggcgtttg aaaccccgga ag                                      22

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ttagcagtcg aagtacaatt cg                                      22

<210> SEQ ID NO 9
<211> LENGTH: 40
<212> TYPE: DNA
<213> ORGANISM: Artificial Sequence
<220> FEATURE:

<223> OTHER INFORMATION: primer

<400> SEQUENCE: 9
ggggatcctc tagagtcgac cttgattgat catgtcgagg        40

<210> SEQ ID NO 10
<211> LENGTH: 42
<212> TYPE: DNA
<213> ORGANISM: Artificial Sequence
<220> FEATURE:
<223> OTHER INFORMATION: primer

<400> SEQUENCE: 10
ctatcggcta gctaagtgaa ggtgactcct cattgacatg gg        42

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
cccatgtcaa tgaggagtca ccttcactta gctagccgat ag        42

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
gcttgcatgc ctgcaggtcg actctggcga ggtccatatg        40

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
tgcaaggcga ttaagttggg taac        24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gaaacagcta tgaccatgat tacg        24

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
cgatgacatg gttcgcaacc tcg        23

-continued

```
<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gagcaaaccc tcacatctca                                                    20

<210> SEQ ID NO 17
<211> LENGTH: 46
<212> TYPE: DNA
<213> ORGANISM: Artificial Sequence
<220> FEATURE:
<223> OTHER INFORMATION: primer

<400> SEQUENCE: 17
gcatcgagcc acacgctcca gtgaacaagg acctctacga actacc                       46

<210> SEQ ID NO 18
<211> LENGTH: 46
<212> TYPE: DNA
<213> ORGANISM: Artificial Sequence
<220> FEATURE:
<223> OTHER INFORMATION: primer

<400> SEQUENCE: 18
ggtagttcgt agaggtcctt gttcactgga gcgtgtggct cgatgc                       46

<210> SEQ ID NO 19
<211> LENGTH: 46
<212> TYPE: DNA
<213> ORGANISM: Artificial Sequence
<220> FEATURE:
<223> OTHER INFORMATION: primer

<400> SEQUENCE: 19
gcatcgagcc acacgctcca gtggaaaagg acctctacga actacc                       46

<210> SEQ ID NO 20
<211> LENGTH: 46
<212> TYPE: DNA
<213> ORGANISM: Artificial Sequence
<220> FEATURE:
<223> OTHER INFORMATION: primer

<400> SEQUENCE: 20
ggtagttcgt agaggtcctt ttccactgga gcgtgtggct cgatgc                       46

<210> SEQ ID NO 21
<211> LENGTH: 46
<212> TYPE: DNA
<213> ORGANISM: Artificial Sequence
<220> FEATURE:
<223> OTHER INFORMATION: primer

<400> SEQUENCE: 21
gcatcgagcc acacgctcca gtgcacaagg acctctacga actacc                       46

<210> SEQ ID NO 22
<211> LENGTH: 46
<212> TYPE: DNA
<213> ORGANISM: Artificial Sequence
<220> FEATURE:
<223> OTHER INFORMATION: primer
```

<400> SEQUENCE: 22
ggtagttcgt agaggtcctt gtgcactgga gcgtgtggct cgatgc         46

<210> SEQ ID NO 23
<211> LENGTH: 46
<212> TYPE: DNA
<213> ORGANISM: Artificial Sequence
<220> FEATURE:
<223> OTHER INFORMATION: primer

<400> SEQUENCE: 23
gcatcgagcc acacgctcca gtgagcaagg acctctacga actacc         46

<210> SEQ ID NO 24
<211> LENGTH: 46
<212> TYPE: DNA
<213> ORGANISM: Artificial Sequence
<220> FEATURE:
<223> OTHER INFORMATION: primer

<400> SEQUENCE: 24
ggtagttcgt agaggtcctt gctcactgga gcgtgtggct cgatgc         46

<210> SEQ ID NO 25
<211> LENGTH: 46
<212> TYPE: DNA
<213> ORGANISM: Artificial Sequence
<220> FEATURE:
<223> OTHER INFORMATION: primer

<400> SEQUENCE: 25
gcatcgagcc acacgctcca gtggtcaagg acctctacga actacc         46

<210> SEQ ID NO 26
<211> LENGTH: 46
<212> TYPE: DNA
<213> ORGANISM: Artificial Sequence
<220> FEATURE:
<223> OTHER INFORMATION: primer

<400> SEQUENCE: 26
ggtagttcgt agaggtcctt gaccactgga gcgtgtggct cgatgc         46

<210> SEQ ID NO 27
<211> LENGTH: 46
<212> TYPE: DNA
<213> ORGANISM: Artificial Sequence
<220> FEATURE:
<223> OTHER INFORMATION: primer

<400> SEQUENCE: 27
gcatcgagcc acacgctcca gtgaacaagg acctcttcga actacc         46

<210> SEQ ID NO 28
<211> LENGTH: 46
<212> TYPE: DNA
<213> ORGANISM: Artificial Sequence
<220> FEATURE:
<223> OTHER INFORMATION: primer

<400> SEQUENCE: 28
ggtagttcga agaggtcctt gttcactgga gcgtgtggct cgatgc         46

<210> SEQ ID NO 29
<211> LENGTH: 1434

<212> TYPE: DNA
<213> ORGANISM: Artificial Sequence
<220> FEATURE:
<223> OTHER INFORMATION: Synthetic sequence Corynebacterium glutamicum
    ATCC13032 Glutamine synthetase n.t

<400> SEQUENCE: 29

```
gtggcgtttg aaaccccgga agaaattgtc aagttcatca aggatgaaaa cgtcgagttc        60
gttgacgttc gattcaccga ccttcccggc accgagcagc acttcagcat cccagctgcc       120
agcttcgatg cagatacaat cgaagaaggt ctcgcattcg acggatcctc gatccgtggc       180
ttcaccacga tcgacgaatc tgacatgaat ctcctgccag acctcggaac ggccaccctt       240
gatccattcc gcaaggcaaa gaccctgaac gttaagttct tcgttcacga tccttt cacc      300
cgcgaggcat tctcccgcga cccacgcaac gtggcacgca aggcagagca gtacctggca       360
tccaccggca ttgcagacac ctgcaacttc ggcgccgagg ctgagttcta cctcttcgac       420
tccgttcgct actccaccga gatgaactcc ggcttctacg aagtagatac cgaagaaggc       480
tggtggaacc gtggcaagga aaccaacctc gacggcaccc caaacctggg cgcaaagaac       540
cgcgtcaagg gtggctactt cccagtagca ccatacgacc aaaccgttga cgtgcgcgat       600
gacatggttc gcaacctcgc agcttccggc ttcgctcttg agcgtttcca ccacgaagtc       660
ggtggcggac agcaggaaat caactaccgc ttcaacacca tgctccacgc ggcagatgat       720
atccagacct tcaagtacat catcaagaac accgctcgcc tccacggcaa ggctgcaacc       780
ttcatgccta agccactggc tggcgacaac ggttccggca tgcacgctca ccagtccctc       840
tggaaggacg gcaagccact cttccacgat gagtccggct acgcaggcct gtccgacatc       900
gcccgctact acatcggcgg catcctgcac cacgcaggcg ctgttctggc gttcaccaac       960
gcaaccctga actcctacca ccgtctggtt ccaggcttcg aggctccaat caacctggtg      1020
tactcacagc gcaaccgttc cgctgctgtc cgtatcccaa tcaccggatc caacccgaag      1080
gcaaagcgca tcgaattccg cgctccagac ccatcaggca acccataccc t gggctttgca    1140
gcgatgatga tggccggcct cgacggcatc aagaaccgca tcgagccaca cgctccagtg      1200
gacaaggacc tctacgaact accaccagag gaagctgcat ccattccaca ggcaccaacc      1260
tccctggaag catccctgaa ggcactgcag gaagacaccg acttcctcac cgagtctgac      1320
gtcttcaccg aggatctcat cgaggcgtac atccagtaca agtacgacaa cgagatctcc      1380
ccagttcgcc tgcgcccaac cccgcaggaa ttcgaattgt acttcgactg ctaa            1434
```

MODIFIED POLYPEPTIDE OF GLUTAMINE SYNTHETASE AND METHOD OF PRODUCING L-GLUTAMINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_477USPC_SEQUENCE_LISTING.txt. The text file is 31.1 KB, was created on Oct. 18, 2021, and is being submitted electronically via EFS-Web.

TECHNICAL FIELD

The present disclosure relates to a modified polypeptide of glutamine synthetase having enhanced activity and a method of producing L-glutamine using the same.

BACKGROUND ART

L-Glutamine is an amino acid widely used in pharmaceuticals, cosmetics, and health functional foods, such as therapeutic agents for digestive troubles, liver function enhancers, brain function enhancers, immune enhancers, medicines for stomach ulcer, medicines for alcoholism, cosmetic moisturizers, nutritional supplements for athletes, and nutritional supplements for patients.

*Corynebacterium glutamicum* and *Escherichia coli* have been used as representative microorganisms for production of L-glutamine. In the L-glutamine biosynthesis pathway, L-glutamate is produced by glutamate dehydrogenase using α-keto glutamic acid, which is produced via glycolysis and the tricarboxylic acid cycle (TCA), as a precursor, and L-glutamine is ultimately produced via a reaction by way of glutamine synthetase.

For production of L-glutamine with a high concentration, it is very important to optimize expression of glutamine synthetase and enhance the activity thereof. A divalent metal ion is required for activation of glutamine synthetase, and the activity is inhibited by glycine, alanine, tryptophan, histidine, glucosamine-6-phosphate, cytidine-3-phosphate, and the like. The activity is also inhibited by adenylation of the 405th amino acid. According to a previous study, it has been reported that the activity inhibited by adenylation was restored by substituting tyrosine at the 405th position with phenylalanine (EP 1229121 B1). However, there is still a need to develop a method of producing L-glutamine with high efficiency.

DISCLOSURE

Technical Problem

With this background, as a result of intensive efforts to develop microorganisms having enhanced L-glutamine producing ability, the present inventors have found a modified polypeptide of glutamine synthetase capable of increasing production of L-glutamine, thereby completing the present disclosure.

Technical Solution

The present disclosure provides a modified polypeptide having glutamine synthetase activity, wherein an amino acid corresponding to the $401^{st}$, $402^{nd}$, or $404^{th}$ position of an amino acid sequence of SEQ ID NO: 1 is substituted with a different amino acid.

The present disclosure provides a polynucleotide encoding the modified polypeptide.

The present disclosure provides a microorganism including the modified polypeptide or the polynucleotide encoding the modified polypeptide.

The present disclosure provides a method of producing L-glutamine, the method including culturing the microorganism of the present disclosure in a culture medium.

Advantageous Effects

When the novel modified polypeptide having enhanced glutamine synthetase activity according to the present disclosure is used, the production of glutamine may be increased without a decrease in growth rate compared to a wild-type strain having glutamine synthetase activity, and thus the modified polypeptide may be widely used for mass production of glutamine.

BEST MODE

The present disclosure will be described in detail. Meanwhile, each description and embodiment disclosed in the present disclosure may be applied to different descriptions and embodiments herein. In other words, all combinations of various components disclosed in the present disclosure are included within the scope of the present disclosure. Furthermore, the scope of the present disclosure should not be limited by the descriptions provided below.

Those skilled in the art will recognize or be able to ascertain, using no more than routine experimentation, many equivalents to specific embodiments of the present disclosure. Such equivalents are intended to be encompassed in the scope of the following claims.

An aspect of the present disclosure provides a glutamine synthetase variant prepared by substituting an amino acid corresponding to the $401^{st}$, $402^{nd}$, or $404^{th}$ position of an amino acid sequence of glutamine synthetase with a different amino acid.

Specifically, the aspect of the present disclosure provides a modified polypeptide having glutamine synthetase activity, wherein an amino acid corresponding to the $401^{st}$, $402^{nd}$, or $404^{th}$ position of an amino acid sequence of SEQ ID NO: 1 is substituted with a different amino acid.

As used herein, the term "variant", "modified polypeptide", or "modified protein (enzyme)" may be used interchangeably.

As used herein, the term "glutamine synthetase" refers to an enzyme that converts glutamic acid and ammonia into glutamine in the presence of ATP in microorganisms. For example, the glutamine synthetase may be encoded by glnA gene, without being limited thereto. In view of the objects of the present disclosure, any protein having the activity for converting glutamic acid and ammonia into glutamine may be used regardless of the origin thereof, and enzymes derived from any organisms (plants, microorganisms, and the like) may be used, without being limited thereto. The glutamine synthetase may be an enzyme derived from a microorganism belongs to the genus *Corynebacterium* or a variant thereof, e.g., an enzyme derived from *Corynebacterium glutamicum*, *Corynebacterium ammoniagenes*, *Brevibacterium lactofermentum*, *Brevibacterium flavum*, *Coryne-* bacterium thermoaminogenes, Corynebacterium efficiens, or Corynebacterium stationis, or a variant thereof, but is not limited thereto.

Specifically, the glutamine synthetase may have the amino acid sequence of SEQ ID NO: 1 or an amino acid sequence having a homology or identity of 80% or more and less than 100% therewith, but the amino acid sequence is not limited thereto as long as the glutamine synthetase activity is obtained thereby. More specifically, the glutamine synthetase of the present disclosure may include a polypeptide having an amino acid sequence having at least 80%, 85%, 90%, 95%, 96%, 97%, 98%, or 99% homology or identity with the amino acid sequence of SEQ ID NO: 1. Also, it is obvious that any accessory protein having deletion, modification, substitution, or addition of one or several amino acids in the amino acid sequence is within the scope of the present disclosure as long as the amino acid sequence retains the above-described homology or identity and an equivalent effect to that of the protein.

As used herein, the term "modified polypeptide having glutamine synthetase activity" or "glutamine synthetase variant" refers to a polypeptide having changed glutamine synthetase activity by substituting a part of an amino acid sequence of a polypeptide having glutamine synthetase activity with a different amino acid. Specifically, the modified polypeptide may be a modified polypeptide having various sequences with glutamine synthetase activity prepared by substituting an amino acid corresponding to the $401^{st}$, $402^{nd}$, or $404^{th}$ position of the amino acid sequence of SEQ ID NO: 1 with a different amino acid.

The "$N^{th}$ position" may include the $N^{th}$ position and a position of an amino acid corresponding to the $N^{th}$ position. Specifically, the $N^{th}$ position may include a corresponding amino acid position of a polypeptide having the same activity as that of the target protein. More specifically, the amino acid sequence of the polypeptide having the same activity as that of the target protein may be the amino acid sequence of SEQ ID NO: 1 or an amino acid sequence having at least 98% identity therewith, and the $401^{st}$, $402^{nd}$, or $404^{th}$ position of the amino acid sequence of SEQ ID NO: 1 may include a position of an amino acid corresponding to the $401^{st}$, $402^{nd}$, or $404^{th}$ position in an amino acid sequence having a homology or identity of 80% or more and less than 100% with the amino acid sequence of SEQ ID NO: 1.

The amino acid position corresponding to the $N^{th}$ position or the corresponding amino acid position of the polypeptide having the same activity as that of the target protein may be determined using the Needleman-Wunsch algorithm (document: Needleman and Wunsch, 1970, *J. Mol. Biol.* 48:443-453), specifically version 5.0.0 or later, as implemented in the Needleman program of the EMBOSS package (EMBOSS: The European Molecular Biology Open Software Suite, document: [Rice et al., 2000, *Trends Genet.* 16:276-277]). Parameters used therefor may be a gap open penalty of 10, a gap extension penalty of 0.5, and an EBLOSUM62 (EMBOSS of BLOSUM62 version) substitution matrix.

An amino acid residue at the amino acid position corresponding to the $N^{th}$ position or the corresponding amino acid position of the polypeptide having the same activity as that of the target protein may be determined by alignment of multiple polypeptide sequences using several computer programs including, but not limited to, MUSCLE (multiple sequence comparison by log-expectation; version 3.5 or later; document: [Edgar, 2004, *Nucleic Acids Research* 32:1792-1797]), MAFFT (version 6.857 or later; document: [Katoh and Kuma, 2002, *Nucleic Acids Research* 30:3059-3066]; document: [Katoh et al., 2005, *Nucleic Acids Research* 33:511-518]; document: [Katoh and Toh, 2007, *Bioinformatics* 23:372-374]; document: [Katoh et al., 2009, *Methods in Molecular Biology* 537:39-64]; document: [Katoh and Toh, 2010, *Bioinformatics* 26:1899-1900]), and EMBOSS EMMA using ClustalW (1.83 or later; document: [Thompson et al., 1994, *Nucleic Acids Research* 22:4673-4680]), using respective default parameters thereof.

When a relationship between polypeptides cannot be detected by conventional sequence-based comparison (document: [Lindahl and Elofsson, 2000, *J. Mol. Biol.* 295:613-615]), other pairwise sequence comparison algorithms may be used. Higher sensitivity in sequence-based searching may be obtained using search programs using probabilistic representations of polypeptide families (profiles) in a search database. For example, the PSI-BLAST program generates profiles through an iterative database search process and is capable of detecting remote homologs (document: [Atschul et al., 1997, *Nucleic Acids Res.* 25:3389-3402]). Even a high sensitivity may be obtained when the family or superfamily for the polypeptide has one or more representatives in the protein structure database. Programs such as GenTHREADER (document: [Jones, 1999, *J. Mol. Biol.* 287:797-815]; and document: [McGuffin and Jones, 2003, *Bioinformatics* 19:874-881]) utilize information from a variety of sources (PSI-BLAST, secondary structure prediction, structural alignment profiles, and solvation potentials) as input into a neural network that predicts the structural folding for a query sequence. Similarly, a method disclosed in a document [Gough et al., 2000, *J. Mol. Biol.* 313:903-919] may be used to align a sequence of an unknown structure with the superfamily models present in the SCOP database. These alignments may in turn be used to generate a homology, similarity, or identity model for the polypeptide, and such models may be assessed for accuracy using a variety of tools developed for that purpose.

The "different amino acid" is not particularly limited as long as the amino acid is different from the amino acid of each position before substitution. Specifically, the amino acid may include at least one amino acid selected from the group consisting of glycine, alanine, arginine, valine, leucine, methionine, isoleucine, threonine, asparagine, glutamine, proline, serine, tryptophan, phenylalanine, histidine, cysteine, tyrosine, lysine, aspartic acid, and glutamic acid, but is not limited thereto.

The "amino acids" are classified into four types: acidic, basic, polar (hydrophilic), and non-polar (hydrophobic) amino acids according to properties of side chains.

The variant may be a protein in which an amino acid at each position of the amino acid sequence of SEQ ID NO: 1 is substituted with at least one amino acid selected from the group consisting of: a non-polar amino acid, e.g., glycine (G), alanine (A), valine (V), leucine (L), isoleucine (I), methionine (M), phenylalanine (F), tryptophan (W), and proline (P); a polar amino acid, e.g., serine (S), threonine (T), cysteine (C), tyrosine (Y), aspartic acid (D), and glutamine (Q); an acidic amino acid, e.g., asparagine (N) and glutamic acid (E); and a basic amino acid, e.g., lysine (K), arginine (R), and histidine (H), without being limited thereto.

Specifically, the amino acid corresponding to the $401^{st}$ position may be substituted with an acidic amino acid or a polar amino acid, the amino acid corresponding to the $402^{nd}$ position may be substituted with a basic amino acid, and the amino acid corresponding to the $404^{th}$ position may be substituted with a non-polar amino acid, without being limited thereto.

More specifically, the amino acid corresponding to the $401^{st}$ position may be substituted with asparagine, glutamic acid, or serine, the amino acid corresponding to the $402^{nd}$ position may be substituted with histidine, and the amino acid corresponding to the $404^{th}$ position may be substituted with valine, without being limited thereto.

In the present disclosure, the modified polypeptide in which an amino acid corresponding to the $401^{st}$, $402^{nd}$, or $404^{th}$ position of the amino acid sequence of SEQ ID NO: 1 is substituted with a different amino acid may have one of the amino acid sequences of SEQ ID NOS: 2 to 6.

Specifically, a modified polypeptide in which the amino acid corresponding to the $401^{st}$ position is substituted with asparagine may have the amino acid sequence of SEQ ID NO: 2, a modified polypeptide in which the amino acid corresponding to the $401^{st}$ position is substituted with glutamic acid may have the amino acid sequence of SEQ ID NO: 3, and a modified polypeptide in which the amino acid corresponding to the $401^{st}$ position is substituted with serine may have the amino acid sequence of SEQ ID NO: 4.

In addition, a modified polypeptide in which the amino acid corresponding to the $402^{nd}$ position is substituted with histidine may have the amino acid sequence of SEQ ID NO: 5, and a modified polypeptide in which the amino acid corresponding to the $404^{th}$ position is substituted with valine may have the amino acid sequence of SEQ ID NO: 6.

The modified polypeptide may be a modified polypeptide having glutamine synthetase activity and a sequence homology of 80% or more and less than 100% with the amino acid sequence of SEQ ID NO: 1, but is not limited thereto. Specifically, the modified polypeptide of the present disclosure may be one having at least 80%, 90%, 95%, 96%, 97%, 98% or 99% homology with the amino acid sequence of SEQ ID NO: 1, and it is obvious that any protein including deletion, modification, substitution, or addition of one or several amino acids in the amino acid sequence in addition to substitution at the $401^{st}$, $402^{nd}$, or $404^{th}$ position is within the scope of the present disclosure as long as the amino acid sequence retains the above-described homology and an effect equivalent to that of the protein.

In the present disclosure, although expressed as a "protein having an amino acid sequence as set forth in a predetermined SEQ ID NO", it is obvious that any protein including deletion, modification, substitution, conservative substitution, or addition of one or several amino acids may be used in the present disclosure as long as the protein has activity identical or equivalent to that of the protein consisting of the amino acid sequence of the SEQ ID NO. For example, addition of a sequence not changing the function of the protein in the forward or reverse direction of the amino acid sequence, a naturally occurring mutation, a silent mutation thereof, or a conservative substitution thereof is not excluded as long as activity identical or equivalent to that of the protein is obtained, and it is obvious that such addition of sequence or mutation is within the scope of the present disclosure.

The modified polypeptide may include a polypeptide obtained by conservative substitution and/or modification of at least one amino acid different from that of the recited sequence while retaining functions or properties of the protein in addition to the substitution of an amino acid at the particular position with a different amino acid.

As used herein, the term "conservative substitution" refers to substitution of one amino acid with another amino acid having similar structural and/or chemical properties. Such amino acid substitution may generally occur based on similarity of polarity, charge, solubility, hydrophobicity, hydrophilicity, and/or amphipathic nature of a residue. In general, conservative substitution has little or no influence on activity of a protein or a polypeptide.

Also, variants having at least one modified amino acid in addition to the amino acid at the above-described position may have deletion or addition of amino acids that have minimal influence on properties and a secondary structure of the polypeptide. For example, the polypeptide may be conjugated with a signal (or leader) sequence of the N-terminus of a protein which co-translationally or post-translationally directs transfer of the protein. In addition, the polypeptide may be conjugated with another sequence or linker to identify, purify, or synthesize the polypeptide.

In addition, the modified polypeptide may include an amino acid sequence having the above-described modification of SEQ ID NO: 1 and/or both the modification of SEQ ID NO: 1 and a homology or identity of 80%, 85%, 90%, 95%, 96%, 97%, 98%, or 99% or more in addition the modification position. That is, the polypeptide may include an amino acid sequence having a homology of 80% or more and less than 100% with one of the sequences of SEQ ID NOS: 2 to 6, but is not limited thereto. Specifically, the modified polypeptide of the present disclosure may include an amino acid sequence having a homology or identity of 80%, 85%, 90%, 95%, 96%, 97%, 98%, or 99% A or more with one of the sequences of SEQ ID NOS: 2 to 6. The modification of SEQ ID NO: 1 is as described above, and the homology or identity thereof may be homology or identity at a position other than the above-described modification.

In view of the objects of the present disclosure, the activity of the modified polypeptide having glutamine synthetase activity may be enhanced compared that of a wild-type. Specifically, the glutamine synthetase activity may be increased and enhanced compared to the wild-type of SEQ ID NO: 1.

As used herein, the term "enhancement" of the activity of the polypeptide refers to an increase in activity of the polypeptide compared to intrinsic activity. The enhancement may be used interchangeably with activation, up-regulation, overexpression, increase, and the like. In this regard, the activation, enhancement, up-regulation, overexpression, and increase may include all of those exhibiting activity that was not originally possessed or exhibiting improved activity compared to intrinsic activity or activity before modification. The "intrinsic activity" refers to activity of a particular polypeptide originally possessed by a parent strain or non-modified microorganism before transformation when the microorganism is transformed by genetic modification caused by a natural or artificial factor. This term may be used interchangeably with "activity before transformation". The "enhancement", "up-regulation", "overexpression", or "increase" of activity of a polypeptide compared to intrinsic activity means that activity and/or concentration (expression level) of a particular polypeptide is improved compared to those originally possessed by a parent strain or non-modified microorganism before transformation.

The enhancement may be achieved by introduction of a foreign polypeptide or enhancement of activity and/or concentration (expression level) of the intrinsic polypeptide. The enhancement of activity of the polypeptide may be identified based on the increase in the degree of activity, the expression level of the polypeptide, or the amount of a product released from the polypeptide.

Enhancement of the polypeptide may be obtained by applying various methods well known in the art, and the methods are not limited as long as the activity of the target polypeptide is enhanced compared to that of the microorganism before modification. Specifically, any genetic engineering and/or protein engineering method well known in the art as routine methods of molecular biology may be used, without being limited thereto (for example, Sitnicka et al. Functional Analysis of Genes. *Advances in Cell Biology.* 2010, Vol. 2. 1-16, Sambrook et al. *Molecular Cloning* 2012, etc.).

Specifically, the enhancement of the polypeptide of the present disclosure may be achieved by:
1) increase in copy number of a polynucleotide encoding the polypeptide in cells;
2) replacement of a gene expression regulatory region on a chromosome encoding the polypeptide with a sequence having higher activity;
3) modification of a nucleotide sequence encoding an initiation codon or 5'-UTR region of a gene transcript encoding the polypeptide;
4) modification of an amino acid sequence of the polypeptide to enhance the activity of the polypeptide;
5) modification of a nucleotide sequence encoding the polypeptide to enhance the activity of the polypeptide (e.g., modification of a nucleotide sequence of a polypeptide gene to encode a modified polypeptide having enhanced activity of the polypeptide);
6) introduction of a foreign polypeptide exhibiting the activity of the polypeptide or a foreign polynucleotide encoding the same;
7) codon optimization of a polynucleotide encoding the polypeptide;
8) modification or chemical modification of an exposed region selected by analyzing a three-dimensional structure of the polypeptide; or
9) any combination of at least two selected from 1) to 8) above, without being limited thereto.

More specifically, the increase in copy number of a polynucleotide encoding the polypeptide in cells of 1) may be achieved by introduction of a vector, which may replicate and function irrespective of a host and is operably linked to a polynucleotide encoding the polypeptide, into a host cell. Alternatively, this may be achieved by introducing one copy or two or more copies of the polynucleotide encoding the polypeptide into the chromosome in a host cell. The introduction of the chromosome may be performed by introducing the vector capable of inserting the polynucleotide into the chromosome of the host into the host cell, but is not limited thereto. The vector is as described above.

The replacement of a gene expression regulatory region (or expression regulatory sequence) on a chromosome encoding the polypeptide with a sequence having higher activity of 2) may be, for example, mutation on the sequence by deletion, insertion, non-conservative substitution, conservative substitution, or any combination thereof to further enhance the activity of the expression regulatory region or replacement with a sequence having higher activity. The expression regulatory region may include, but is not limited to, a promoter, an operator sequence, a sequence encoding a ribosome binding site, and a sequence regulating termination of transcription and translation. For example, the replacement may be replacement of an intrinsic promoter with a stronger promoter, but is not limited thereto.

Examples of the stronger promoter known in the art may include CJ1 to CJ7 promoters (U.S. Pat. No. 7,662,943 B2), lac promoter, trp promoter, trc promoter, tac promoter, Lambda phage PR promoter, PL promoter, tet promoter, gapA promoter, SPL7 promoter, SPL13(sm3) promoter (U.S. patent Ser. No. 10/584,338 B2), 02 promoter (U.S. patent Ser. No. 10/273,491 B2), tkt promoter, and yccA promoter, but are not limited thereto.

The modification of a nucleotide sequence encoding an initiation codon or 5'-UTR region of a gene transcript encoding the polypeptide of 3) may be, for example, substitution with a nucleotide sequence encoding another initiation codon with a higher expression level of the polypeptide than an intrinsic initiation codon, but is not limited thereto.

The modification of an amino acid sequence or a polynucleotide sequence of 4) and 5) may be modification on the amino acid sequence of the polypeptide or the polynucleotide sequence encoding the polypeptide by deletion, insertion, non-conservative substitution, conservative substitution, or any combination thereof to enhance the activity of the polypeptide, or replacement with an amino acid sequence or a polynucleotide sequence modified to have higher activity or an amino acid sequence or a polynucleotide sequence modified to increase the activity, but is not limited thereto. The replacement may be performed by inserting the polynucleotide into the chromosome, specifically by homologous recombination, but is not limited thereto. A vector used in the case may further include a selection marker to identify insertion into the chromosome. The selection marker is as described above.

The introduction of a foreign polypeptide exhibiting the activity of the polypeptide of 6) may be introduction of a foreign polynucleotide encoding the polypeptide exhibiting activity identical/similar to that of the polypeptide into a host cell. The origin and sequence of the foreign polynucleotide are not particularly limited as long as the polynucleotide exhibits activity identical/similar to that of the polypeptide. Any transformation method appropriately selected by those skilled in the art may be used for the introduction. As the introduced polynucleotide is expressed in the host cell, the polypeptide is produced, thereby increasing the activity of the polypeptide.

The codon optimization of a polynucleotide encoding the polypeptide of 7) may be codon optimization of an intrinsic polynucleotide to increase transcription or translation in a host cell, or codon optimization of a foreign polynucleotide for optimizing transcription and translation thereof in a host cell.

The modification or chemical modification of an exposed region selected by analyzing a three-dimensional structure of the polypeptide of 8) may be, for example, modification or chemical modification of an exposed region to be modified or chemically modified by comparing sequence information of a polypeptide to be analyzed with a database that stores sequence information of existing proteins, determining a template protein candidate according to similarity of the sequences, and identifying the structure based thereon.

Such enhancement of the activity of the polypeptide activity may be an increase in the activity or concentration of the expressed polypeptide compared to the activity or concentration of a polypeptide expressed in wild-type microorganisms or microorganism strains before transformation or an increase in the amount of a product obtained from the polypeptide, without being limited thereto.

For example, it was confirmed that the increase in the glutamine producing ability of the modified polypeptide of the present disclosure increased compared to the wild-type indicating enhanced glutamine synthetase activity (Tables 1 to 3).

In the microorganism of the present disclosure, modification of the polynucleotide as a whole or in part may be induced by (a) homologous recombination using a vector for chromosomal insertion into the microorganism or genome editing using an engineered nuclease (e.g., CRISPR-Cas9) and/or (b) treatment with light such as UV rays and radioactive rays and/or a chemical substance, without being limited thereto. A method of modifying the gene in whole or in part may include a DNA recombination technique. For example, a part of or the entire gene may be deleted by inducing homologous recombination by injecting a nucleotide sequence or vector including a nucleotide sequence having a homology with a target gene into the microorganism. The injected nucleotide sequence or vector may include a dominant selection marker, without being limited thereto.

Another aspect of the present disclosure provides a polynucleotide encoding the modified polypeptide, or a vector including the polynucleotide.

The amino acid sequence of SEQ ID NO: 1, the glutamine synthetase, and the modified polypeptide having glutamine synthetase activity are as described above.

As used herein, the term "polynucleotide" refers to a DNA or RNA strand having a certain minimum length as a polymer of nucleotides in which nucleotide monomers are linked to each other in the form of a long chain by covalent bonds, more specifically a polynucleotide fragment encoding the modified protein.

The polynucleotide of the present disclosure may include any polynucleotide sequence encoding the modified polypeptide having glutamine synthetase activity of the present disclosure without limitation. Specifically, the polynucleotide of the present disclosure may include any sequence encoding the modified polypeptide having glutamine synthetase activity in which the amino acid corresponding to the $401^{st}$, $402^{nd}$, or $404^{th}$ position of the amino acid sequence of SEQ ID NO: 1 is substituted with a different amino acid without limitation. For example, the polynucleotide may have a polynucleotide sequence encoding one of the amino acid sequences of SEQ ID NOS: 2 to 6, without being limited thereto. Various modifications may be made in a coding region of the polynucleotide within a range not changing the amino acid sequence of the protein due to codon degeneracy or in consideration of a codon preferred by an organism in which the protein is to be expressed. Thus, it is obvious that the polynucleotide may include a polynucleotide that may be translated into the polypeptide consisting of the amino acid sequence or a polypeptide having a homology or identity therewith, more specifically a homology or identity of 80% or more and less than 100%, due to codon degeneracy.

In addition, the polynucleotide may include any sequence hybridized with a probe constructed using known gene sequences, e.g., a nucleotide sequence entirely or partially complementary to the polynucleotide under stringent conditions, to encode the modified polypeptide having glutamine synthetase activity, without limitation.

The term "stringent conditions" refers to conditions allowing specific hybridization between polynucleotides. Such conditions are disclosed in detail in known documents (J. Sambrook et al., *Molecular Cloning, A Laboratory Manual*, $2^{nd}$ Edition, Cold Spring Harbor Laboratory press, Cold Spring Harbor, New York, 1989; F. M. Ausubel et al., *Current Protocols in Molecular Biology*, John Wiley & Sons, Inc., New York 9.50-9.51, 11.7-11.8).

For example, the stringent conditions may include conditions for performing hybridization between polynucleotides having a high homology or identity, e.g., a homology or identity of 70% or more, 75% or more, 80% or more, 85% or more, 90% or more, 95% or more, 96% or more, 97% or more, 98% or more, or 99% or more, without performing hybridization between polynucleotides having a homology or identity lower than the above homologies or identities, or washing once, specifically twice or three times, under general washing conditions for Southern hybridization at a salt concentration and temperature of 60° C., 1×SSC, 0.1% SDS, specifically 60° C., 0.1×SSC, 0.1% SDS, and more specifically 68° C., 0.1×SSC, 0.1% SDS.

Hybridization requires that two polynucleotides have complementary sequences, although bases may mismatch according to the degree of stringency of hybridization. The term "complementary" is used to describe the relationship between bases of nucleotides capable of hybridizing with each other. For example, with respect to DNA, adenosine is complementary to thymine, and cytosine is complementary to guanine. Thus, the polynucleotide of the present disclosure may include not only a substantially similar nucleic acid sequence but also a nucleic acid fragment isolated but complementary to the entire sequence.

Specifically, a polynucleotide having a homology or identity with the polynucleotide of the present disclosure may be detected using the above-described hybridization conditions including a hybridization process at a $T_m$ value of 55° C. Also, the $T_m$ value may be, but is not limited to, 60° C., 63° C., or 65° C., and may be appropriately adjusted by those skilled in the art according to the intended purposes.

An appropriate degree of stringency for hybridization of the polynucleotides may depend on lengths, and the degree of complementarity of the polynucleotides and parameters thereof are well known in the art (e.g., Sambrook et al., described above).

As used herein, the term "homology" or "identity" refers to the degree of relatedness between two given amino acid sequences or nucleotide sequences and may be expressed as a percentage. The terms homology and identity may often be used interchangeably.

Sequence homology or identity of conserved polynucleotides or polypeptides may be determined using a standard alignment algorithm, and default gap penalties established by a program may be used together therewith. Substantially, homologous or identical sequences may generally hybridize with each other as a whole or in part under moderate or highly stringent conditions. It is obvious that the hybridization includes hybridization with a polynucleotide including a common codon or a codon in consideration of codon degeneracy in the polynucleotide.

The sequence homology, similarity, or identity between two polynucleotides or polypeptide sequences may be determined using any computer algorithm known in the art such as the "FASTA" program using default parameters disclosed by Pearson et al. (1988) *Proc. Natl. Acad. Sci. USA* 85:2444. Alternatively, the homology, similarity, or identity may be determined by using the Needleman-Wunsch algorithm (Needleman and Wunsch, 1970, *J. Mol. Biol.* 48:443-453) as implemented in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J. et al., *Nucleic Acids Research* 12:387 (1984)), BLASTP, BLASTN, FASTA (Atschul, S. F. et al., J MOLEC BIOL 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST of the National Center for Biotechnology Information database, or ClustalW.

The homology, similarity, or identity between polynucleotides or polypeptides may be determined by comparing sequence information using the GAP computer program as introduced by, for example, Needleman et al. (1970), *J Mol Biol.* 48:443 as disclosed by Smith and Waterman, *Adv. Appl. Math* (1981) 2:482. Briefly, the GAP program defines similarity as the number of aligned symbols (i.e., nucleotides or amino acids) which are similar, divided by the total number of symbols in a shorter of two sequences. Default parameters for the GAP program may include: (1) a binary comparison matrix (containing a value of 1 for identity and 0 for non-identity) and a weighted comparison matrix of Gribskov et al. (1986) *Nucl. Acids Res.* 14:6745 disclosed in Schwartz and Dayhoff, eds., *Atlas Of Protein Sequence And Structure*, National Biomedical Research Foundation, pp. 353-358 (1979) (or the EDNAFULL (EMBOSS version of NCBI NUC4.4) substitution matrix); (2) a penalty of 3.0 for each gap and an additional 0.10 penalty for each symbol in each gap (or a gap open penalty of 10, and a gap extension penalty of 0.5); and (3) no penalty for end gaps.

Another aspect of the present disclosure provides a microorganism including: the modified polypeptide having glutamine synthetase activity of the present disclosure; the polynucleotide encoding the modified polypeptide of the present disclosure; or the vector of the present disclosure.

The vector of the present disclosure may be an expression vector for expressing the polynucleotide in a host cell, but is not limited thereto.

The vector of the present disclosure may include a DNA construct containing a nucleotide sequence of a polynucleotide encoding the target polypeptide operably linked to an expression regulatory region (or expression regulatory sequence) suitable for expressing the target polypeptide in a suitable host. The expression regulatory region may include a promoter capable of initiating transcription, any operator sequence for regulating the transcription, a sequence encoding a suitable mRNA ribosome binding site, and a sequence for regulating termination of transcription and translation. Once transformed into a suitable host cell, the vector may replicate or function independently from a host genome, or may integrate into the genome.

The vector used in the present disclosure is not particularly limited, and any vector known in the art may be used. Examples of conventional vectors may include a natural or recombinant plasmid, cosmid, virus and bacteriophage. For example, pWE15, M13, MBL3, MBL4, IXII, ASHII, APII, t10, t11, Charon4A, and Charon21A may be used as a phage vector or a cosmid vector. As a plasmid vector, pDZ type, pBR type, pUC type, pBluescriptII type, pGEM type, pTZ type, pCL type, and pET type may be used. Specifically, pDZ, pDC, pDCM2, pACYC177, pACYC184, pCL, pECCG117, pUC19, pBR322, pMW118, and pCC1BAC vectors may be used.

For example, the polynucleotide encoding the target polypeptide may be inserted into a chromosome using a vector for chromosomal insertion. The insertion of the polynucleotide into the chromosome may be performed by way of any method known in the art, for example, homologous recombination, without being limited thereto. The polynucleotide may further include a selection marker to confirm the chromosomal insertion. The selection marker is used to select cells that are transformed with the vector, that is, to confirm insertion of a desired nucleic acid molecule, and examples of the selection marker may include markers providing selectable phenotypes, such as drug resistance, nutrient requirement, resistance to cytotoxic agents, or expression of surface polypeptide. Only cells expressing the selection marker are able to survive or to show different phenotypes under the environment treated with a selective agent, and thus the transformed cells may be selected.

The microorganism may be a microorganism having L-glutamine producing ability.

As used herein, the "microorganism (or strain)" includes both wild-type microorganisms and microorganisms including natural or artificial genetic modification, such as microorganisms having a particular mechanism weakened or enhanced via introduction of an exogenous gene or enhancement or inactivation of an endogenous gene and including genetic modification to produce a target polypeptide, protein, or product.

Specifically, the microorganism including the modified polypeptide having glutamine synthetase activity of the present disclosure may be a microorganism naturally having L-glutamine producing ability or a microorganism prepared by providing the L-glutamine producing ability to a parent strain unable to produce L-glutamine.

As used herein, the term "microorganism including the modified polypeptide having glutamine synthetase activity" may refer to a recombinant microorganism expressing the modified polypeptide of the present disclosure.

For example, the microorganism refers to a microorganism including a polynucleotide encoding the modified polypeptide having glutamine synthetase activity, or a host cell or microorganism transformed with a polynucleotide encoding the modified polypeptide or a vector including the same to be able to express the modified polypeptide.

As used herein, the term "glutamine" is an amino acid widely used in pharmaceuticals, cosmetics, and health foods, such as therapeutic agents for digestive troubles, liver function enhancers, brain function enhancers, immune enhancers, medicines for stomach ulcer, medicines for alcoholism, cosmetic moisturizers, nutritional supplements for athletes, and nutritional supplements for patients. The glutamine may be produced from glutamic acid and ammonia by glutamine synthetase in the presence of ATP. That is, in the present disclosure, since the activity of glutamine synthetase is enhanced by including the modified polypeptide having the glutamine synthetase activity, glutamine producing ability of a microorganism including the same may be enhanced.

Specifically, in the present disclosure, the glutamine may be L-glutamine. Throughout the specification, the term "glutamine" may be used interchangeably with "L-glutamine".

As used herein, the term "transformation" refers to a process of introducing a vector including a polynucleotide encoding a target polypeptide into a host cell or microorganism in such a way that the polypeptide encoded by the polynucleotide is expressed in the host cell. The transformed polynucleotide may be either in a form inserted into the chromosome of the host cell or in a form located outside the chromosome as long as the protein is expressed in the host cell. In addition, the polynucleotide includes DNA and/or RNA encoding the target polypeptide. The polynucleotide may be introduced into the host cell in any form as long as the polynucleotide is introduced into the host cell and the polypeptide is expressed therein. For example, the polynucleotide may be introduced into the host cell in the form of an expression cassette that is a gene construct including all of the essential elements required for self-replication. The expression cassette may generally include a promoter operably linked to the polynucleotide, a transcription termination signal, a ribosome binding site, and a translation termination signal. The expression cassette may be in the form of a self-replicable expression vector. Also, the polynucleotide may be introduced into the host cell in its original form and operably linked to a sequence required for the expression in the host cell, without being limited thereto.

In addition, as used herein, the term "operably linked" refers to an operable linkage between a promoter sequence, which enables initiation and mediation of transcription of a polynucleotide encoding the target variant of the present disclosure, and the polynucleotide sequence.

In view of the objects of the present disclosure, the microorganism may specifically be a microorganism expressing the modified polypeptide having glutamine synthetase activity in which an amino acid corresponding to the $401^{st}$, $402^{nd}$, or $404^{th}$ position of the amino acid sequence of SEQ ID NO: 1 is substituted with a different amino acid. Specifically, the microorganism may be a microorganism expressing the modified polypeptide having glutamine synthetase activity by substituting the amino acid corresponding to the $401^{st}$ position from the N-terminus of the amino acid sequence of SEQ ID NO: 1 with asparagine, glutamic acid, or serine, by substituting the amino acid corresponding to the $402^{nd}$ position with histidine, or by substituting the amino acid corresponding to the $404^{th}$ position with valine. More specifically, the microorganism may be a microorganism expressing the modified polypeptide having glutamine synthetase activity by substituting the amino acid at the $401^{st}$ position from the N-terminus of the amino acid sequence of SEQ ID NO: 1 with asparagine, glutamic acid, or serine, by substituting the amino acid at the $402^{nd}$ position with histidine, or by substituting the amino acid at the $404^{th}$ position with valine, without being limited thereto. For example, the microorganism may be a microorganism expressing a modified polypeptide including modification at the $401^{st}$, $402^{nd}$, or $405^{th}$ position and having a homology or identity of 80% or more and less than 100% with the sequence of SEQ ID NO: 1 or a microorganism expressing a modified polypeptide having one of the amino acid sequences of SEQ ID NOS: 2 to 6. Since the microorganism includes the modified polypeptide having glutamine synthetase activity in which the amino acid is substituted at the above-described position, the activity of glutamine synthetase is enhanced, thereby increasing the production of glutamine without inhibiting growth.

In the present disclosure, the microorganism including the modified polypeptide may be a microorganism belonging to the genus *Enterobacter*, the genus *Escherichia*, the genus *Erwinia*, the genus *Serratia*, the genus *Pseudomonas*, the genus *Providencia*, the genus *Corynebacterium*, and the genus *Brevibacterium*, but types thereof are not particularly limited thereto. More specifically, the microorganism may be a microorganism belonging to the genus *Corynebacterium*.

In the present disclosure, the "microorganism belonging to the genus *Corynebacterium*" may be *Corynebacterium glutamicum*, *Corynebacterium ammoniagenes*, *Brevibacterium lactofermentum*, *Brevibacterium flavum*, *Corynebacterium thermoaminogenes*, or *Corynebacterium efficiens*, but is not limited thereto. In an embodiment, the microorganism belonging to the genus *Corynebacterium* may be *Corynebacterium glutamicum*.

The microorganism of the present disclosure may include any microorganisms capable of expressing the modified polypeptide having glutamine synthetase activity of the present disclosure via various known methods as well as introduction of the polynucleotide or vector.

Another aspect of the present disclosure provides a method of producing L-glutamine, the method including culturing a microorganism including a modified polypeptide having glutamine synthetase activity, in which an amino acid corresponding to the $401^{st}$, $402^{nd}$, or $404^{th}$ position of the amino acid sequence of SEQ ID NO: 1 is substituted with a different amino acid or a polynucleotide encoding the modified polypeptide (the microorganism of the present disclosure), in a culture medium.

Also, in an embodiment of the present disclosure, the microorganism may be a microorganism belonging to the genus *Corynebacterium*, and the microorganism belonging to the genus *Corynebacterium* may be *Corynebacterium glutamicum*.

In the present disclosure, the term "culturing" refers to growing the microorganism in an appropriately adjusted environment. In the present disclosure, a culturing process may be performed in an appropriate medium and culturing conditions well known in the art. The culturing process may be easily used after adjustment according to a strain being selected by one of ordinary skill in the art. Specifically, the culturing of the microorganism may be performed in a batch process, a continuous process, and/or a fed-batch process, but is not limited thereto.

As used herein, the term "culture medium" refers to a mixture containing nutrients required for culturing the microorganism of the present disclosure as main ingredients, and which supplies nutrients and growth factors including water which are essential for survival and growth. Specifically, although the culture medium used to culture of the *Corynebacterium glutamicum* strain and other culturing conditions according to the present disclosure are not particularly limited as long as the culture medium is commonly used for culturing microorganisms, the microorganism of the present disclosure may be cultured in a common culture medium containing an appropriate carbon source, nitrogen source, phosphorus source, inorganic compound, amino acid, and/or vitamin under aerobic conditions while adjusting temperature, pH, and the like.

Specifically, a culture medium for a strain belonging to the genus *Corynebacterium* is disclosed in a document ["Manual of Methods for General Bacteriology" by the American Society for Bacteriology (Washington D.C., U.S.A., 1981)].

In the present disclosure, examples of the carbon source may include: carbohydrates such as glucose, sucrose, lactose, fructose, and maltose; sugar alcohols such as mannitol and sorbitol; organic acids such as pyruvic acid, lactic acid, and citric acid; and amino acids such as glutamic acid, methionine, and lysine. In addition, natural organic nutrients such as starch hydrolysates, molasses, blackstrap molasses, rice bran, cassava, sugar cane bagasse, and corn steep liquor may be used, and specifically, carbohydrates such as glucose and sterile pretreated molasses (i.e., molasses converted to reduced sugars) may be used, and suitable amounts of any other carbon sources may also be used without limitation. These carbon sources may be used alone or in a combination of at least two thereof, but are not limited thereto.

As the nitrogen sources, inorganic nitrogen sources such as ammonia, ammonium sulfate, ammonium chloride, ammonium acetate, ammonium phosphate, ammonium carbonate, and ammonium nitrate; and organic nitrogen sources such as amino acids, e.g., glutamic acid, methionine, and glutamine, peptone, NZ-amine, meat extract, yeast extract, malt extract, corn steep liquor, casein hydrolysate, fish or degradation products thereof, and defatted soybean cake or degradation products thereof may be used. These nitrogen sources may be used alone or in a combination of at least two thereof, without being limited thereto.

As the phosphorus sources, monopotassium phosphate, dipotassium phosphate, or sodium-containing salts corresponding thereto may be used. As the inorganic compounds, sodium chloride, calcium chloride, iron chloride, magnesium sulfate, iron sulfate, manganese sulfate, calcium carbonate, and the like may be used. The culture medium may further include amino acids, vitamins, and/or appropriate precursors. These components or precursors may be added to the culture medium in a batch or continuous process. However, the present disclosure is not limited thereto.

In addition, during the culturing process of the microorganism of the present disclosure, compounds such as ammonium hydroxide, potassium hydroxide, ammonia, phosphoric acid, and sulfuric acid may be added to the culture medium in an appropriate manner to adjust the pH of the culture medium. In addition, a defoaming agent such as a fatty acid polyglycol ester may be added during the culturing process to inhibit generation of foam. Also, oxygen or an oxygen-containing gas may be injected into the culture medium to maintain the aerobic conditions of the culture medium, or nitrogen, hydrogen, or carbon dioxide gas or no gas may be injected to maintain an anaerobic and microaerobic conditions, without being limited thereto.

The culturing may be performed at a culture temperature 20° C. to 40° C., specifically 25° C. to 40° C., for about 10 hours to 160 hours, but is not limited thereto.

L-Glutamine produced during the culturing of the present disclosure may be released into the culture medium or remain in the cells.

The method of producing L-glutamine according to the present disclosure may further include preparing the microorganism of the present disclosure, preparing a culture medium for culturing the strain, or any combination thereof (regardless of order, in any order), for example, before the culturing step.

The method of producing L-glutamine according to the present disclosure may further include recovering L-glutamine from the culture medium after culturing (culture medium where the culturing is performed) or the microorganism of the present disclosure. The recovering step may further be included after the culturing step.

The recovering may be collecting desired L-glutamine using the culturing method of the present disclosure, e.g., an appropriate method known in the art such as a batch, continuous, or fed-batch method. For example, centrifugation, filtration, treatment with a protein precipitating agent (salting out), extraction, ultrasonic disintegration, ultrafiltration, dialysis, various chromatographic methods such as molecular sieve chromatography (gel permeation), adsorption chromatography, ion-exchange chromatography, and affinity chromatography, high-performance liquid chromatography (HPLC), any combination thereof may be used, and the desired L-glutamine may be recovered from the culture medium or the microorganism using an appropriate method well known in the art.

In addition, the method of producing L-glutamine of the present disclosure may further include purifying the L-glutamine. The purifying step may be performed using an appropriate method well known in the art. In an embodiment, when the method of producing L-glutamine of the present disclosure includes both the recovering and purifying steps, the recovering and purifying steps may be performed continuously or discontinuously regardless of order, or may be performed simultaneously or as one integrated step, without being limited thereto.

In the method of the present disclosure, the variant, the polynucleotide, the vector, the microorganism, the L-glutamine, and the like are as described above.

Another aspect of the present disclosure provides a method of increasing L-glutamine producing ability including modifying a microorganism to express a modified polypeptide having glutamine synthetase activity in which an amino acid corresponding to the $401^{st}$ position, an amino acid corresponding to the $402^{nd}$ position, or an amino acid corresponding to the $404^{th}$ position of the amino acid sequence SEQ ID NO: 1 is substituted with a different amino acid.

Another aspect of the present disclosure provides a use for increasing L-glutamine producing ability of a microorganism expressing: the modified polypeptide; a polynucleotide encoding the modified polypeptide; a vector including the polynucleotide; or at least one thereof.

The modified polypeptide, the different amino acid, the polynucleotide, the vector, the microorganism, and the L-glutamine are as described above.

Another aspect of the present disclosure provides a composition for producing L-glutamine including: the modified polypeptide having glutamine synthetase activity; a polynucleotide encoding the modified polypeptide; a vector including the polynucleotide; or a microorganism expressing at least one thereof or a culture solution thereof.

The modified polypeptide, the polynucleotide, the vector, the microorganism, and the L-glutamine are as described above.

The composition for producing L-glutamine may refer to a composition capable of producing L-glutamine using the modified polypeptide having glutamine synthetase activity of the present disclosure. The composition may include the modified polypeptide having glutamine synthetase activity or any components capable of operating the modified polypeptide having glutamine synthetase activity without limitation. The modified polypeptide having glutamine synthetase activity may be in a form included in a vector such that a gene operably linked thereto is expressed in a host cell into the vector is introduced.

The composition may further include a cryoprotectant or an excipient. The cryoprotectant or excipient may be a substance which does not occur naturally or a naturally occurring substance, but is not limited thereto.

As another example, the cryoprotectant or excipient may be a substance that the microorganism does not naturally come into contact with, or a substance that is not naturally included with the microorganism at the same time, but is not limited thereto.

MODE FOR INVENTION

Hereinafter, the present disclosure will be described in more detail with reference to the following examples. However, the following examples are merely presented to exemplify the present disclosure, and the scope of the present disclosure is not limited thereto.

Example 1. Construction of Library of Vector for Introduction of Mutation into ORF of glnA Gene A library was constructed in the following method to discover variants having increased expression levels or activity of glnA gene that encodes glutamine synthetase of *Corynebacterium glutamicum*.

First, a GenemorphII Random Mutagenesis Kit (Stratagene) was used to introduce 0 to 4.5 mutations per kb into a DNA fragment (1,434 bp) including glnA gene (1,434 bp). Error-prone PCR was performed using a chromosome of *Corynebacterium glutamicum* ATCC13032 (WT) as a template and using a primer set of SEQ ID NOS: 7 and 8. Specifically, the PCR was performed using a reaction solution including the chromosome of a WT strain (500 ng), primers 7 and 8 (each having 125 ng), Mutazyme II reaction buffer (1Y), dNTP mix (40 mM), and Mutazyme II DNA polymerase (2.5 U) under the following conditions: denaturation at 94° C. for 2 minutes; 25 cycles of denaturation at 94° C. for 1 minute, annealing at 56° C. for 1 minute, and polymerization at 72° C. for 2 minutes; and then polymerization at 72° C. for 10 minutes.

The amplified gene fragment was ligated to a pCRII vector using a TOPO TA Cloning Kit (Invitrogen), and *E. coli* DH5a was transformed therewith and plated on an LB solid medium containing kanamycin (25 mg/L). Twenty transformed colonies were selected, and plasmids were obtained therefrom. As a result of analyzing nucleotide sequences, it was confirmed that mutation was introduced into different positions at a frequency of 0.5 mutations/kb. Finally, about 10,000 transformed *E. coli* colonies were obtained, and plasmids were extracted therefrom and named pTOPO-glnA(mt) library.

Example 2: Preparation of glnA-Deleted Strain and Screening of glnA-Mutated Strain In order to construct a strain in which the glnA gene was deleted from a wild-type *Corynebacterium glutamicum* ATCC13032, a pDZ-ΔglnA vector in which the glnA gene was deleted was prepared as follows. Specifically, the vector was constructed in a form where DNA fragments (each having 1000 bp) located at the 5'- and 3'-ends of the glnA gene are ligated to a pDZ vector (Korean Patent No. 2009-0094433).

Based on a nucleotide sequence of glnA gene of SEQ ID NO: 29, primers of SEQ ID NOS: 10 and 11 prepared by inserting a restriction enzyme SalI recognition site into the 5' fragment and 3' fragment and primers of SEQ ID NOS: 9 and 12 at positions spaced apart therefrom by 1000 bp, respectively, were synthesized.

The 5'-end gene fragment was prepared via PCR using a chromosome of *Corynebacterium glutamicum* ATCC13032 as a template with a primer set of SEQ ID NOS: 9 and 10. In the same manner, the 3'-end gene fragment of the glnA gene was prepared via PCR using a primer set of SEQ ID NOS: 11 and 12. The PCR was performed under the following conditions: denaturation at 94° C. for 2 minutes, 30 cycles of denaturation at 94° C. for 1 minute, annealing at 56° C. for 1 minute, and polymerization at 72° C. for 40 seconds, and then polymerization at 72° C. for 10 minutes.

Meanwhile, after treatment with the restriction enzyme SalI, the pDZ vector heat-treated at 65° C. for 20 minutes was ligated with the DNA fragments to be inserted amplified by the PCR using an Infusion Cloning Kit, *E. coli* DH5a was transformed therewith and then plated on an LB solid medium containing kanamycin (25 mg/L). Colonies transformed with the vector into which the target gene was inserted were selected via PCR using a primer set of SEQ ID NOS: 13 and 14, and then a plasmid was obtained using a plasmid extraction method known in the art and named pDZ-ΔglnA.

*Corynebacterium glutamicum* ATCC13032 was transformed with the prepared pDZ-ΔglnA vector by way of an electric-pulse method (Van der Rest et al., Appl. Microbial. Biotechnol. 52:541-545, 1999) to prepare a glnA gene-deleted strain by homologous chromosomal recombination. The strain in which the glnA gene-deleted was deleted was named *Corynebacterium glutamicum* ATCC13032::ΔglnA.

Also, the ATCC13032::ΔglnA strain was transformed with a pTOPO-glnA(mt) library by way of an electric-pulse method and plated on a complex plate medium containing kanamycin (25 mg/L), and about 100 colonies were obtained. The 100 strains were subjected to an L-glutamine producing ability test. Each of the obtained 100 stains was inoculated into a 250 mL corner-baffle flask containing 25 mL of a glutamine production medium and cultured while shaking at 32° C. for 48 hours at 200 rpm. 1 mL of a seed culture was inoculated into a 250 mL corner-baffle flask containing 24 mL of an L-glutamine production medium and cultured while shaking at 30° C. for 48 hours at 200 rpm.

*Corynebacterium glutamicum* ATCC13032 and ATCC13032::ΔglnA strains were used as controls. After completion of the culturing, L-glutamine present in a supernatant of a cell-free medium was measured using a YSI 7100 Multiparameter Bioanalytical System (YSI Inc.). Strains having L-glutamine producing ability superior to that of the ATCC13032::ΔglnA strain and a higher concentration of L-glutamine than the ATCC13032 were selected, and concentrations of glutamine in the culture solutions are shown in Table 1. The selected strains were named ATCC13032::glnA(mt)-1 to 3. The other ninety-seven colonies had lower L-glutamine concentrations compared to those of ATCC13032 that was used as a control.

TABLE 1

| Analysis of L-glutamine-producing ability of ATCC13032-derived ATCC13032::glnA(mt) | | |
|---|---|---|
| | Strain | L-Glutamine (g/L) |
| Control | ATCC13032 | 0.89 |
| | ATCC13032::ΔglnA | 0.77 |
| Experimental | ATCC13032::glnA(mt)-1 | 1.25 |
| | ATCC13032::glnA(mt)-2 | 0.99 |
| | ATCC13032::glnA(mt)-3 | 1.05 |

As shown in Table 1, it was confirmed that the ATCC13032::glnA(mt)-1 had improved L-glutamine producing ability by about 40%, the ATCC13032::glnA(mt)-2 had improved L-glutamine producing ability by about 11%, and the ATCC13032::glnA(mt)-3 had improved L-glutamine producing ability by about 18% compared to the control.

Example 3: Identification of Nucleotide Sequence of Three glnA-Mutated Strains

In order to identify the glnA gene nucleotide sequence of the three selected strains ATCC13032::glnA(mt)-1 to 3, DNA fragments including the glnA gene in the chromosome were amplified via PCR using the primer set of SEQ ID NOS: 7 and 8 of Example 1. The PCR was performed under the following conditions: denaturation at 94° C. for 2 minutes; 30 cycles of denaturation at 94° C. for 1 minute, annealing at 56° C. for 1 minute, and polymerization at 72° C. for 40 seconds; and then polymerization at 72° C. for 10 minutes.

As a result of analyzing nucleotide sequences of the amplified gene, it was confirmed that the three strains are variants: ATCC13032::glnA(mt)-1 is a variant in which the $1201^{st}$ to $1203^{rd}$ positions of a nucleotide sequence of SEQ ID NO: 5 are changed from GAC to ACC so that aspartic acid, which is the $401^{st}$ amino acid from the N-terminal, is substituted with asparagine, ATCC13032::glnA(mt)-2 is a variant in which the $1204^{th}$ to $1206^{th}$ positions of the nucleotide sequence of SEQ ID NO: 5 are changed from AAG to CAC so that lysine, which is the $402^{nd}$ amino acid from the N-terminal, is substituted with histidine, and ATCC13032::glnA(mt)-3 is a variant in which the $1210^{th}$ to $1212^{th}$ positions of the nucleotide sequence of SEQ ID NO: 5 are changed from CTC to GTC so that leucine, which is the $404^{th}$ amino acid, is substituted with valine. Among the three strains, the ATCC13032::glnA(mt)-1 strain exhibiting a higher production of L-glutamine and a similar growth rate compared to ATCC13032 was selected as a glutamine synthetase activity-enhancing strain.

Example 4: Construction of Various Strains in which $401^{st}$ Amino Acid (Aspartic Acid) is Substituted with Different Amino Acid Since it was confirmed that the $401^{st}$ amino acid is an important position for the enzymatic activity in Example 3, attempts have been made to substitute the $401^{st}$ amino acid of the amino acid sequence as set forth in SEQ ID NO: 1 with amino acids other than the aspartic acid of the wild-type.

In order to introduce heterologous substitution of four types including D401N confirmed in Example 3, respective recombinant vectors therefor were constructed by way of the following method.

First, primers of SEQ ID NOS: 15 and 16 were synthesized using a genome DNA extracted from the WT strain as a template by inserting a restriction enzyme SalI recognition site into the 5' fragment and 3' fragment at positions spaced apart from the $1201^{st}$ to $1203^{rd}$ positions of the glnA gene by about 600 bp, respectively. In order to introduce heterologous substitution of the four types, primers of SEQ ID NOS: 17 to 26 were synthesized for substitution of the $1201^{st}$ to $1203^{rd}$ positions of the nucleotide sequence of the glnA gene.

Also, with respect to Y405F, which is a previously known mutation for deadenylation of the glnA gene, primers of SEQ ID NOS: 27 and 28 were synthesized for comparison of the glutamine producing ability.

Specifically, the pDZ-glnA(D401N) plasmid was constructed in a form where DNA fragments (each having 600 bp) located at the 5'- and 3'-ends of the glnA gene are ligated to the pDZ vector (Korean Patent No. 2009-0094433). The 5'-end gene fragment of the glnA gene was constructed via PCR using the chromosome of the WT strain as a template and using the primer set of SEQ ID NOS: 15 and 18. The PCR was performed under the following conditions: denaturation at 94° C. for 2 minutes; 30 cycles of denaturation at 94° C. for 1 minute, annealing at 56° C. for 1 minute, and polymerization at 72° C. for 40 seconds; and then polymerization at 72° C. for 10 minutes. In the same manner, the gene fragment located at the 3'-end of the glnA gene was constructed via PCR using the primer set of SEQ ID NOS: 16 and 17. The amplified DNA fragments were purified by using a PCR Purification kit of Quiagen and used as DNA fragments to be inserted for construction of a vector.

Meanwhile, after the pDZ vector treated with the restriction enzyme SalI and heat-treated at 65° C. for 20 minutes was ligated to the DNA fragment for insertion amplified by the PCR using an Infusion Cloning Kit, E. coli DH5a was transformed therewith. The strain was plated on an LB solid medium containing kanamycin (25 mg/L). Colonies transformed with a vector inserted with a desired gene were selected via PCR using a primer set of SEQ ID NOS: 13 and 14, and a plasmid was obtained using a plasmid extraction method well known in the art. The plasmid was named pDZ-glnA(D401N).

In the same manner, pDZ-glnA(D401E) was constructed using a primer set of SEQ ID NOS: 15 and 20 and a primer set of SEQ ID NOS: 16 and 19, and pDZ-glnA(D401S) was constructed using a primer set of SEQ ID NOS: 15 and 24 and a primer set of SEQ ID NOS: 16 and 23. Also, pDZ-glnA(Y405F) was constructed using a primer set of SEQ ID NOS: 15 and 28 and a primer set of SEQ ID NOS: 16 and 27.

In order to more clearly determine the concentration of glutamine and growth rate in accordance with the introduction of the glnA gene, *Corynebacterium glutamicum* ATCC13032 that produces glutamine was transformed with each of the constructed vectors using an electric-pulse method, and four strains prepared by introducing heterologous substitution into the glnA gene by homologous chromosomal recombination, i.e., ATCC13032::glnA (D401N), ATCC13032::glnA (D401E), ATCC13032::glnA (D401S), and ATCC13032::glnA (Y405F), were constructed. Among them, the ATCC13032::glnA (D401N) was named CA11-4021 and deposited with the Korean Culture Center of Microorganisms (KCCM), recognized as an international depositary authority under the Budapest Treaty, on Dec. 19, 2019, under the accession number KCCM12645P.

Example 5: Analysis of Glutamine-Producing Ability of glnA-Mutated Strain

The four strains constructed in Example 4 above were cultured in the following method to measure glucose consumption rates and glutamine producing ability thereof using the ATCC13032 strain as a control.

First, each of the strains was inoculated into a 250 mL corner-baffle flask containing 25 mL of a seed medium and cultured while shaking at 30° C. for 20 hours at 200 rpm. Then, 1 mL of a seed culture was inoculated into a 250 mL corner-baffle flask containing 24 mL of a production medium and cultured while shaking at 32° C. for 48 hours at 200 rpm. The compositions of the seed medium and the production medium are as follows. After completion of the culturing, the concentrations of L-glutamine were measured using HPLC (Waters 2478). Measurement results of the glutamine producing ability and glucose consumption rates are as shown in Table 2 below.

Seed Medium (pH 7.0)

20 g of glucose, 10 g of peptone, 5 g of yeast extract, 1.5 g of urea, 4 g of $KH_2PO_4$, 8 g of $K2HPO_4$, 0.5 g of $MgSO_4·7H_2O$, 100 μg of biotin, 1000 μg of thiamine HCl, 2000 μg of calcium pantothenate, and 2000 μg of nicotinamide (based on 1 L of distilled water).

Glutamine Production Medium (pH 8.0)

60 g of raw sugar, 45 g of $(NH_4)_2SO_4$, 0.48 g of soybean protein, 50 g of $CaCO_3$, 0.4 g of $MgSO_4·7H_2O$, 1 g of $KH_2PO_4$, 0.2 mg of thiamine hydrochloride, 0.3 mg of biotin, 60 mg of nicotinamide, 10 mg of $FeSO_4·7H_2O$, and 10 mg of $MnSO_4·H_2O$ (based on 1 L of distilled water).

TABLE 2

Analysis of L-glutamine producing ability and glucose consumption rate of ATCC13032-derived ATCC13032::glnA(mt)

| | Strain | L-Glutamine (g/L) | Glucose consumption rate (g/hr) |
|---|---|---|---|
| Control | ATCC13032::AglnA | 0.77 | 4.69 |
| | ATCC13032 | 0.89 | 4.72 |
| | ATCC13032::glnA (D401N) | 1.25 | 4.76 |
| | ATCC13032::glnA (D401E) | 1.19 | 5.16 |
| | ATCC13032::glnA (D401S) | 0.88 | 6.50 |
| Deadenylation mutation | ATCC13032::glnA (Y405F) | 1.20 | 4.45 |

In the case of the strain including the modified polypeptide in which the 401$^{st}$ amino acid of SEQ ID NO: 1 was substituted with a different amino acid, when the substituted amino acid was asparagine (ATCC13032::glnA (D401N)) and glutamic acid (ATCC13032::glnA (D401E)), it was confirmed that the glutamine producing ability was increased by about 40% and 33%, respectively. These results indicate that the glutamine producing ability is improved when compared with the ATCC13032::glnA (Y405F) strain introduced with the glnA deadenylation mutation.

Example 6: Construction of Glutamine-Producing Strain-Based glnA-Mutated Strain

*Corynebacterium glutamicum* KFCC-10680 (Korean Patent No. 10-0048440) strain that is an existing glutamine-producing strain was transformed with pDZ-glnA(D401N), pDZ-glnA(D401E), and pDZ-glnA(Y405F), respectively, in the same manner as in Example 4 by way of an electric-pulse method. Three strains prepared by introducing heterologous substitution into the glnA gene were named KFCC-10680::glnA (D401N), KFCC-10680::glnA (D401E), and KFCC-10680::glnA (Y405F), respectively.

Example 7: Analysis of Glutamine-Producing Ability of Glutamine-Producing Strain-Based glnA-Mutated Strain The three selected strains were cultured as follows to measure glucose consumption rates and glutamine producing ability thereof using the KFCC-10680 strain as a control.

First, each of the strains was inoculated into a 250 mL corner-baffle flask containing 25 mL of a seed medium and cultured while shaking at 30° C. for 20 hours at 200 rpm. Then, 1 mL of a seed culture was inoculated into a 250 mL corner-baffle flask containing 24 mL of a production medium and cultured while shaking at 32° C. for 48 hours at 200 rpm. The compositions of the seed medium and the production medium are as follows. After completion of the culturing, the concentrations of L-glutamine were measured using HPLC (Waters 2478). Measurement results of the glutamine producing ability and glucose consumption rates are as shown in Table 3 below.

Seed Medium (pH 7.0)

20 g of glucose, 10 g of peptone, 5 g of yeast extract, 1.5 g of urea, 4 g of KH$_2$PO$_4$, 8 g of K2HPO$_4$, 0.5 g of MgSO$_4$7H$_2$O, 100 μg of biotin, 1000 μg of thiamine HCl, 2000 μg of calcium pantothenate, and 2000 μg of nicotinamide (based on 1 L of distilled water).

Glutamine Production Medium (pH 8.0)

60 g of raw sugar, 45 g of (NH$_4$)$_2$SO$_4$, 0.48 g of soybean protein, 50 g of CaCO$_3$, 0.4 g of MgSO$_4$·7H$_2$O, 1 g of KH$_2$PO$_4$, 0.2 mg of thiamine hydrochloride, 0.3 mg of biotin, 60 mg of nicotinamide, 10 mg of FeSO$_4$·7H$_2$O, and 10 mg of MnSO$_4$·H$_2$O (based on 1 L of distilled water).

TABLE 3

Analysis of L-glutamine producing ability and glucose consumption rate of KFCC-10680-derived KFCC-10680::glnA(mt)

| | Strain | L-Glutamine (g/L) | Glucose consumption rate (g/hr) |
|---|---|---|---|
| Control | KFCC-10680 | 13.8 | 2.36 |
| | KFCC-10680::glnA (D401N) | 16.7 | 2.38 |
| | KFCC-10680::glnA (D401E) | 15.1 | 2.58 |
| Deadenylation mutation | KFCC-10680::glnA (Y405F) | 14.1 | 2.21 |

In the case of the strain including the modified polypeptide in which the 401$^{st}$ amino acid of SEQ ID NO: 1 was substituted with a different amino acid, when the substituted amino acid was asparagine (KFCC-10680::glnA (D401N)) and glutamic acid (KFCC-10680::glnA (D401E)), it was confirmed that the glutamine producing ability was increased by about 21% and 9%.

These results indicates that the glutamine producing ability was improved when compared with the KFCC-10680::glnA (Y405F) strain introduced with deadenylation mutation of the glnA gene.

The above description of the present disclosure is provided for the purpose of illustration, and it would be understood by those skilled in the art that various changes and modifications may be made without changing the technical conception and essential features of the present disclosure. Thus, it is clear that the above-described embodiments are illustrative in all aspects and do not limit the present disclosure. The various embodiments disclosed herein are not intended to be limiting, with the true scope and spirit being indicated by the following claims. The present disclosure is to be limited only by the terms of the appended claims, along with the full scope of equivalents to which such claims are entitled.

Depositary Authority: Korean Culture Center of Microorganisms (international)

Accession number: KCCM12645P

Date of deposit: 2019 Dec. 19

The invention claimed is:

1. A modified polypeptide having glutamine synthetase activity, wherein the modified polypeptide has a sequence identity of 97% or more and less than 100% with the amino acid sequence of SEQ ID NO: 1, and wherein an amino acid corresponding to position 401, 402, or 404 of the amino acid sequence of SEQ ID NO: 1 is substituted with a different amino acid.

2. The modified polypeptide of claim 1, wherein the amino acid corresponding to position 401 is substituted with asparagine, glutamic acid, or serine.

3. The modified polypeptide of claim 1, wherein the amino acid corresponding to position 402 is substituted with histidine.

4. The modified polypeptide of claim 1, wherein the amino acid corresponding to position 404 is substituted with valine.

5. The modified polypeptide of claim 1, wherein the modified polypeptide comprising SEQ ID NO:1 except that an amino acid corresponding to position 401, 402, or 404 of SEQ ID NO: 1 is substituted with a different amino acid, wherein the modified polypeptide has glutamine synthetase activity.

6. The modified polypeptide of claim 1, wherein the modified polypeptide consist of an amino acid sequence as set forth in SEQ ID NO: 2, SEQ ID NO: 3, SEQ ID NO: 4, SEQ ID NO: 5, or SEQ ID NO: 6.

7. A polynucleotide encoding the modified polypeptide according to claim 1.

8. A microorganism comprising the modified polypeptide according to claim 1 or a polynucleotide encoding the modified polypeptide.

9. The microorganism of claim 8, wherein the microorganism has L-glutamine producing ability.

10. The microorganism of claim 8, wherein the microorganism belongs to the genus *Corynebacterium*.

11. The microorganism of claim 10, wherein the microorganism belonging to the genus *Corynebacterium* is *Corynebacterium glutamicum*.

12. A method of producing L-glutamine, the method comprising culturing a microorganism comprising a modified polypeptide according to claim 1, or a polynucleotide encoding the modified polypeptide, in a culture medium.

13. The method of claim 12, further comprising recovering or isolating L-glutamine from the culture medium or the microorganism.

14. The method of claim 12, wherein the microorganism is a microorganism belonging to the genus *Corynebacterium*.

15. The method of claim 14, wherein the microorganism belonging to the genus *Corynebacterium* is *Corynebacterium glutamicum*.

\* \* \* \* \*